United States Patent [19]

Stein et al.

[11] Patent Number: 5,800,470
[45] Date of Patent: Sep. 1, 1998

[54] RESPIRATORY MUSCLE ELECTROMYOGRAPHIC RATE RESPONSIVE PACEMAKER

[75] Inventors: Paul M. Stein, Maple Grove; Tom D. Bennett, Shoreview; Terrell M. Williams, Brooklyn Park, all of Minn.

[73] Assignee: Medtronic, Inc., Minneapolis, Minn.

[21] Appl. No.: 613,403

[22] Filed: Mar. 11, 1996

Related U.S. Application Data

[63] Continuation of Ser. No. 179,058, Jan. 7, 1994, abandoned.
[51] Int. Cl.$^6$ .................................................. A61N 1/365
[52] U.S. Cl. .............................. 607/20; 607/18; 128/733
[58] Field of Search ........................ 607/17–20, 42, 607/126, 127; 128/718, 733

[56] References Cited

U.S. PATENT DOCUMENTS

| | | | |
|---|---|---|---|
| 3,593,718 | 7/1971 | Krasner et al. | 128/419 PG |
| 4,157,720 | 6/1979 | Greatbatch | 128/419 P |
| 4,253,466 | 3/1981 | Hartlaub et al. | 128/419 PG |
| 4,256,115 | 3/1981 | Bilitch | 128/419 P |
| 4,596,251 | 6/1986 | Plicchi | 128/419 PG |
| 4,624,265 | 11/1986 | Grassi | 607/127 |
| 4,694,830 | 9/1987 | Lekholm | 128/419 PG |
| 4,697,591 | 10/1987 | Lekholm et al. | 128/419 PG |
| 4,702,253 | 10/1987 | Nappholz et al. | 128/419 PG |
| 4,776,338 | 10/1988 | Lekholm et al. | 128/419 PG |
| 4,805,621 | 2/1989 | Heinze et al. | 128/419 PG |
| 4,823,797 | 4/1989 | Heinze et al. | 128/419 PG |
| 4,858,611 | 8/1989 | Elliott | 607/20 |
| 4,961,423 | 10/1990 | Canducci | 128/419 PG |
| 5,201,808 | 4/1993 | Steinhaus et al. | 607/20 |
| 5,273,034 | 12/1993 | Nilsson | 607/18 |

FOREIGN PATENT DOCUMENTS

| | | | |
|---|---|---|---|
| 0226164 | 6/1987 | European Pat. Off. | |
| 0310024 | 4/1989 | European Pat. Off. | 607/20 |

OTHER PUBLICATIONS

Katz et al., "Relationship between electrical activity of the diaphragm and ventilation," Proceedings of the Society for Experimental Biolgical Medicine, vol. 110, pp. 792–794, Jun. 1962.

Ein Herzschrittmacher Mit Belastungsabhangiger Frequenzregulation, Published 1975 in *Biomedische Technik*.

Variation of Cardiac Pacemaker Rate Relative to Respiration, *IEEE Proceedings of 32nd CEMB*, 1979, p. 123.

Variation of Cardiac Pacemaker Rate Relative To Respiration, *IEEE trans. on Biomed. Eng.*, vol. BME-26, No. 9, Sep. 1979, p. 526.

*Primary Examiner*—Marvin M. Lateef
*Assistant Examiner*—Kennedy J. Schaetzle
*Attorney, Agent, or Firm*—Harold R. Patton; Michael B. Atlass

[57] ABSTRACT

A physiologic rate responsive pacer which alters the pacer's escape interval in response to the patient's respiratory minute ventilation derived from the electromyogram of selected respiratory muscle groups. The directly detected electromyogram (EMG) signal is amplified and band passed filtered, processed to remove any electrocardiogram (ECG) or pacing impulse signal, full-wave rectified, processed to develop a moving time average signal from which the peak, the maximal slope, and the average slope of the EMG moving time average may be calculated and processed in conjunction with the inspiratory and expiratory times between successive slope detections of the moving time average EMG to develop a rate control signal representative of minute ventilation. The EMG may be selectively picked up from electrodes implanted in or near the parasternal intercostal muscles, the external intercostal muscles, the internal intercostal muscles, the diaphragm, or any other respiratory muscle such as the scalenes, or the sternocleidomastoid, and coupled to conventionally designed or special configuration pacemaker pulse generators and cardiac pace/sense lead systems.

22 Claims, 13 Drawing Sheets

RESPIRATORY MUSCLE ELECTROMYOGRAPHIC RATE RESPONSIVE PACEMAKER

This application is a continuation of application Ser. No. 08/179,058 filed on Jan. 7, 1994, now abandoned.

BACKGROUND OF THE INVENTION

1. Field of the Invention

This invention relates to cardiac pacemakers and more particularly to rate responsive pacers which alter the pacing rate based on the patient's metabolic demand, specifically respiratory minute ventilation.

2. Description of the Prior Art

In recent years, physiological measurement of increased metabolic energy production to control the pacing rate of a rate responsive pacemaker has involved a variety of sensors and approaches to estimate metabolic demand, including the measurement of blood oxygen saturation, blood pH, central core temperature, blood pressure and its derivatives, cardiac stroke volume, average atrial rate, and physical activity of the patient during exercise.

It is well known that the cardiovascular and respiratory systems increase or decrease their activities in concert to maintain blood gas and metabolic homeostasis. All types of patients tend to increase their respiratory effort with physical, emotional, and mental stress. Ideally, to measure the ventilation of a clinical subject, the actual respired volume, or minute ventilation, should be measured. In clinical practice, this may be performed by utilizing a bulky device, such as a spirometer or pneumotachometer, which must be physically connected to the subject's airways by way of either a mouthpiece, a mask, or an endotracheal tube. Unfortunately, such a system is not practical for chronic implementation in patients. Hence, an index of respiratory effort, which can be sensed internally and continuously, must be developed to provide some sort of measure of the patient's breathing and respiratory effort. Various approaches have been proposed in the past to realize rate responsive pacemakers dependent upon or related in some fashion to respiratory rate of minute volume/minute ventilation.

In the pacing context, one of the first proposals was to employ trans-chest electrodes to develop an impedance plethysmography signal which was converted in a frequency to DC converter to develop a signal to control the pacing rate of an atrial-ventricular sequential pacemaker in U.S. Pat. No. 3,593,718 to Krasner, et al.

Impedance plethysmography employing implantable trans-chest electrodes to generate a rate control signal is also known from U.S. Pat. No. 4,596,251 to Plicchi and Canducci. This prior art pacer derives respiration rate through a thoracic impedance measurement using an auxiliary lead. It has also been proposed to extract an impedance signal that varies as a function of the pleural pressure which, in turn, is a function of the patient's minute volume from electrodes placed in a blood vessel in the vicinity of the patient's pleural cavity in U.S. Pat. No. 4,702,253 to Nappholz, et al.

Other methods of deriving a respiratory signal have been proposed more recently, including the sensing of amplitude variations of the heart action signal as seen from EPO Patent Appln. No. 0 226 164.

The measurement of the voltage drop during the pacing pulse delivery to derive an impedance signal has also been proposed in U.S. Pat. Nos. 4,776,338, 4,694,830 and 4,697,591 to Lekholm, et al. In U.S. Pat. Nos. 4,805,621 and 4,823,797 to Heinze, et al., high and low pass filtering of impedance signals to separate variations to the respiration from variations due to tissue conductance have also been proposed in the processing of impedance plethysmography related signals.

In a further U.S. Pat. No. 4,961,423 to Canducci, it is proposed to employ specific electromyogram or EMG (a graph of electrical signals associated with muscle activity) signal processing circuitry in conjunction with a conventional cardiac pacing lead system to derive a control signal which reflects the patient's respiration as reflected across the electrodes in contact with the patient's heart. By use of specific filtration and signal processing, it is proposed to separate the EMG signal from the electrocardiogram (ECG) signal and pacing stimulation impulse from the aggregate signal picked up across the pacing tip and can electrode pair or across separate electrodes devoted to the detection of the EMG. It is postulated that the myoelectric potentials of the musculature of the thorax are amplitude modulated by the mechanical movements associated with breathing and that the musculature may be modeled as a broad spectrum noise source which is amplitude modulated by respiration. Contributors to the broad spectrum noise source include the mechanical movement or displacement of tip electrode in the heart due in part to physical activity of the patient, the beating of the patient's heart, and the patient's breathing rate mixed with the myoelectric contribution of the diaphragm muscle itself which is closest to the apex of the patient's heart. The signal processing circuitry seeks to detect a frequency shift in the spectral peak in the power spectrum along with a concomitant shift in the harmonics on the theory that the active respiration shifts power into relatively narrow pass bands in the frequency domain due to characteristics of the diaphragm itself acting upon the heart and endocardial lead system.

Other investigators have proposed other sensor techniques and locations. Funke reported on the use of a microphone to monitor intrapleural or intrathoracic pressure in "Ein Herzschrittmacher mit Belastungsabhangiger Frequenzregulation," published in 1975 in Biomedische Tecknik. In this article, Funke also suggested, and rejected, a system based on the detection of electrical activity in the diaphragm or the intercostal musculature.

More recently, Getzel et al described the electronic integration of the diaphragm electromyogram to generate a control signal proportional to respiratory minute volume for use as the controlling physiological input for a pacemaker in "Variation of Cardiac Pacemaker Rate Relative to Respiration," IEEE Proceedings of 32nd CEMB, 1979, p. 123, and "Variation of Cardiac Pacemaker Rate Relative to Respiration," IEEE Trans. on Biomed. Eng., Vol. BME-26, No. 9, September 1979, p. 526.

It remains an important competitive goal in the pacing industry to develop a rate-responsive feature that is based on some single "physiologic" variable. To create a feature for a rate-responsive pacemaker based upon a particular variable, that feature's response must correlate highly to the actual variable under question. In considering respiratory responsive devices, the key variable is minute ventilation. Because it is not practical at this time to measure the minute ventilation of a human with an implantable device, related indices are needed that correlate well with the minute ventilation.

Respiratory muscle EMG's have been widely studied by a large number of researchers and prepared for use as a rate responsive parameter as described above.

SUMMARY OF THE INVENTION

However, in contrast to these prior art teachings, the present invention extracts the EMG signal from a selected set of muscle groups comprising the external intracostals, the internal intercostals, the parasternal intercostals, the diaphragm, or any other respiratory muscle such as the scalenes and sternocleidomastoid, and processes the signals derived therefrom in a moving time average signal processing system from which signals representative of the height or average or maximal slope of the upslope waveform of the moving time average EMG signal are employed in conjunction with the total inspiratory and expiratory times to develop a signal having a high correlation to actual respiratory minute volume through a wide range of patient activities including steady state and transition periods.

The signal processing circuitry of the present invention may be incorporated into pacing systems which include: a conventionally implanted pacemaker and pacing lead system coupled to the heart in conjunction with a separate lead system having distally located electrodes adapted to be coupled to the selected respiratory muscle group; a conventionally implanted pacing pulse generator and lead system with a separate lead and electrode system adapted to be advanced through the patient's venous system and to a location positioning the electrodes adjacent to the selected muscle group; an especially designed pacing system having fixation electrodes adapted to fix the pacing pulse generator directly to the patient's epicardium and having a further lead and electrode system coupled to the selected muscle group for picking up the EMG signal; an especially designed pacing system having electrodes adapted to attach the pacing pulse generator to the selected muscle group and having a pacing lead system adapted to extend to a position of attachment of the pace/sense electrodes on the patient's epicardium or transvenously to a desired location within the patient's heart; a conventionally implanted pacemaker and pacing lead system in conjunction with a separate lead system having electrodes adapted to be passed through an opening in a vein and attached to or placed adjacent to the diaphragm or a selected respiratory muscle group; and a conventionally implanted pacemaker and transvenous pacing lead system, where the transvenous lead system has a miniaturized distal EMG sensing electrode and distal lead segment adapted to be advanced through the relatively thick myocardium of the ventricular apex and to be attached or placed adjacent to the diaphragm. In the latter two cases and variations thereon, the puncture of the vein or right ventricular myocardium by relatively small diameter sensing electrodes and leads may be accomplished by using screw-in electrodes for penetration through the vein or myocardium and attachment to the muscle or diaphragm.

BRIEF DESCRIPTION OF THE DRAWINGS

The above and still further objects, features, and advantages of the present invention will become apparent from the following detailed description of the presently preferred embodiments, taken in conjunction with the accompanying drawings, and, in which.

DESCRIPTION OF THE PREFERRED EMBODIMENTS

Figure 1:
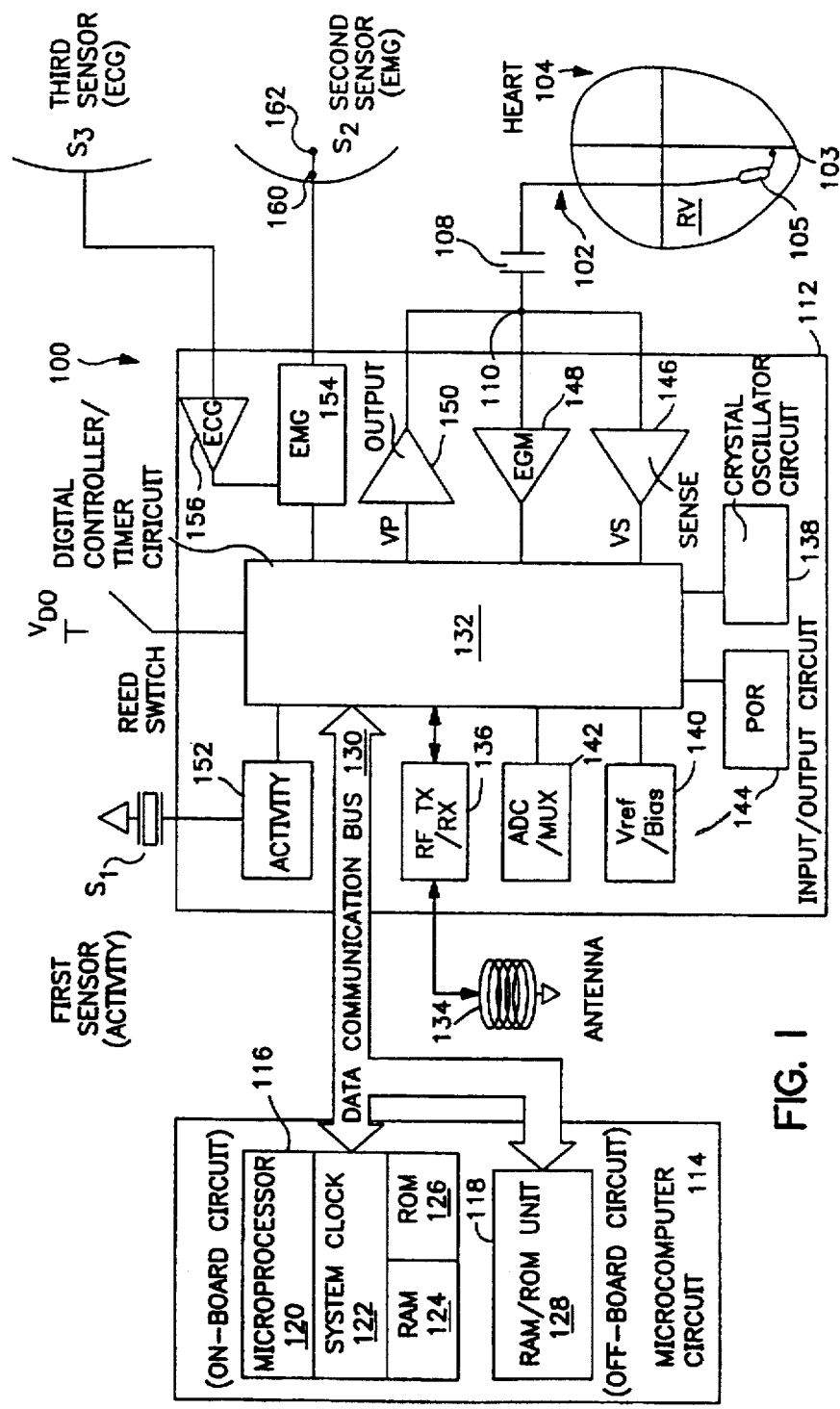
FIG. 1 is a system level block diagram of the circuitry of the present invention.
Figure 2:
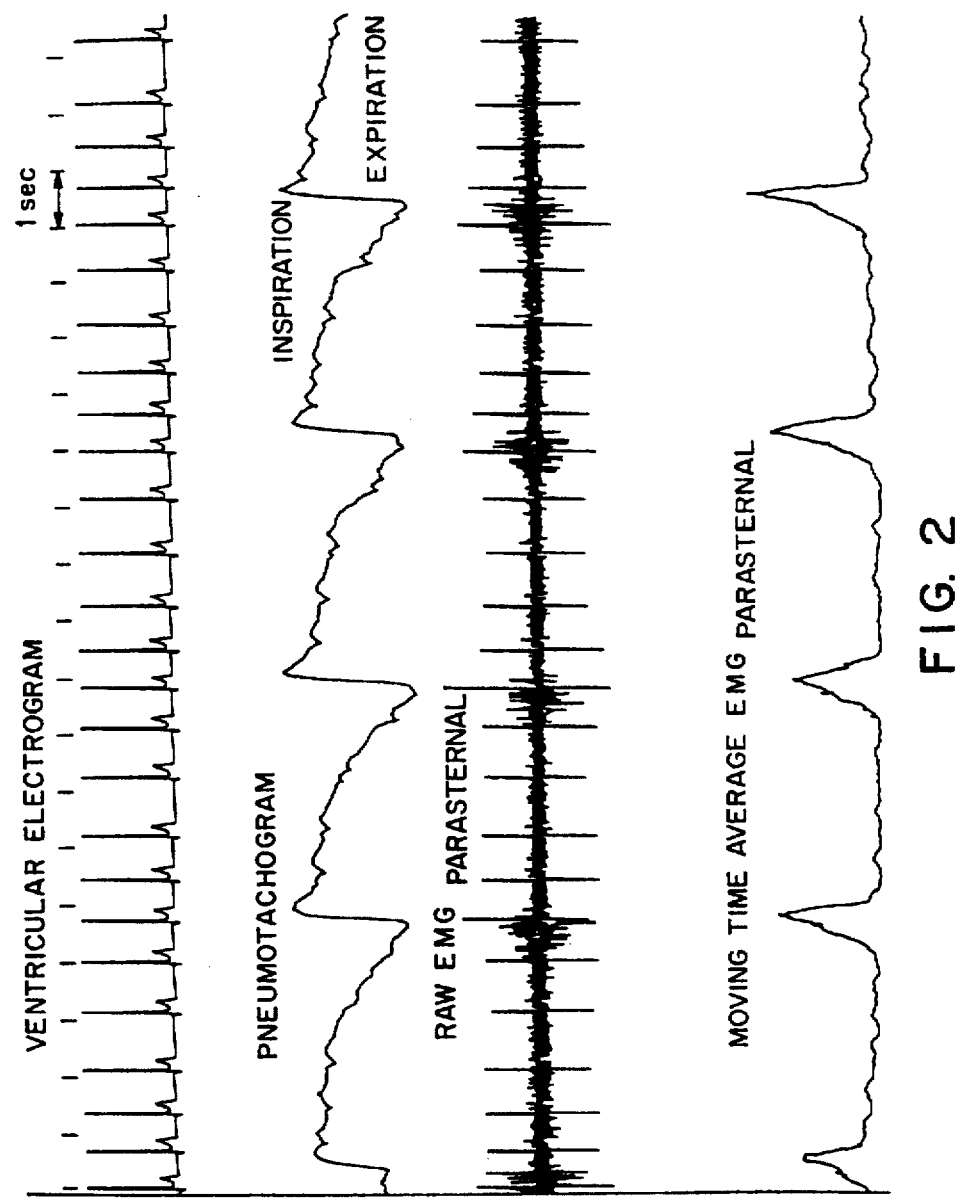
FIG. 2 is a chart recording of the ventricular electrogram, pneumotachographic airflow, raw parasternal intercostal electromyogram, and moving time average electromyogram of a dog during air inhalation.
Figure 3:
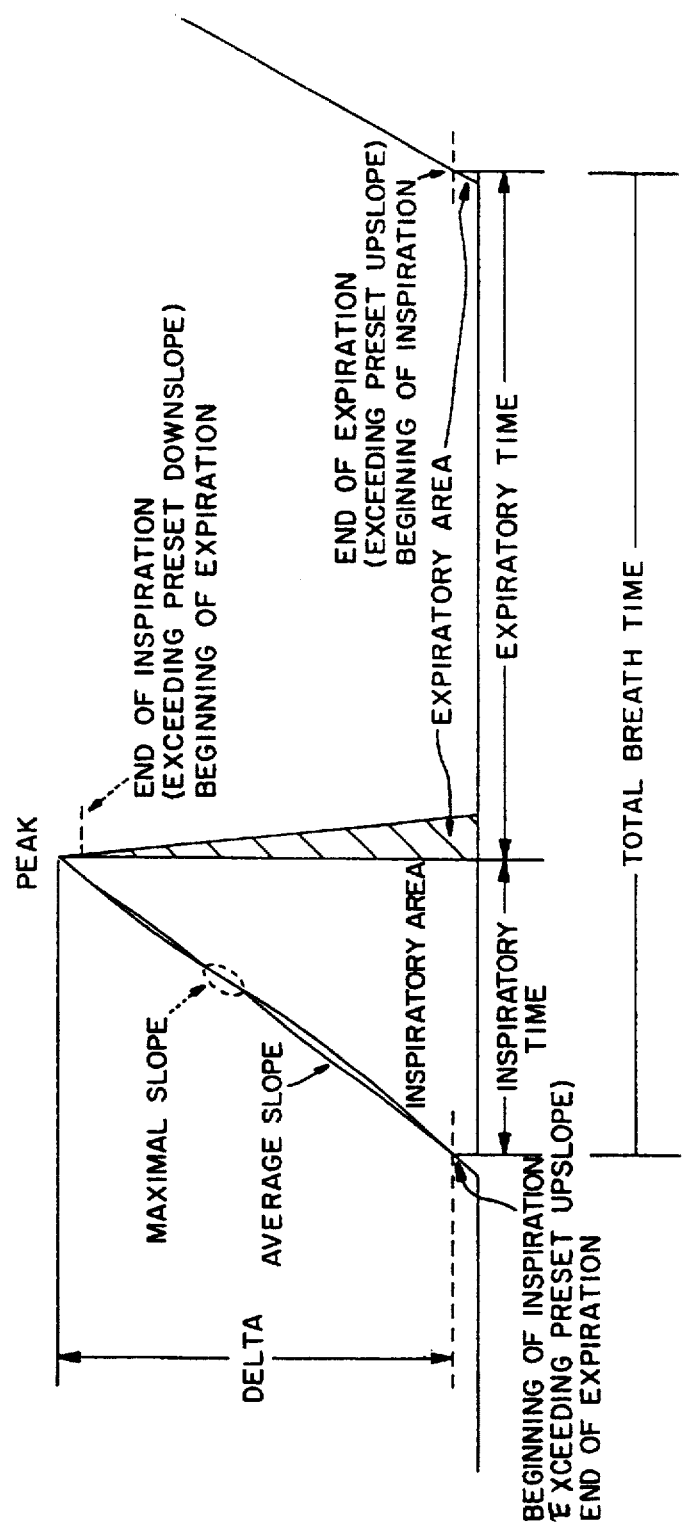
FIG. 3 depicts threshold, timing, and measurement determinations of the moving time average electromyogram by the signal process software.
Figure 4:
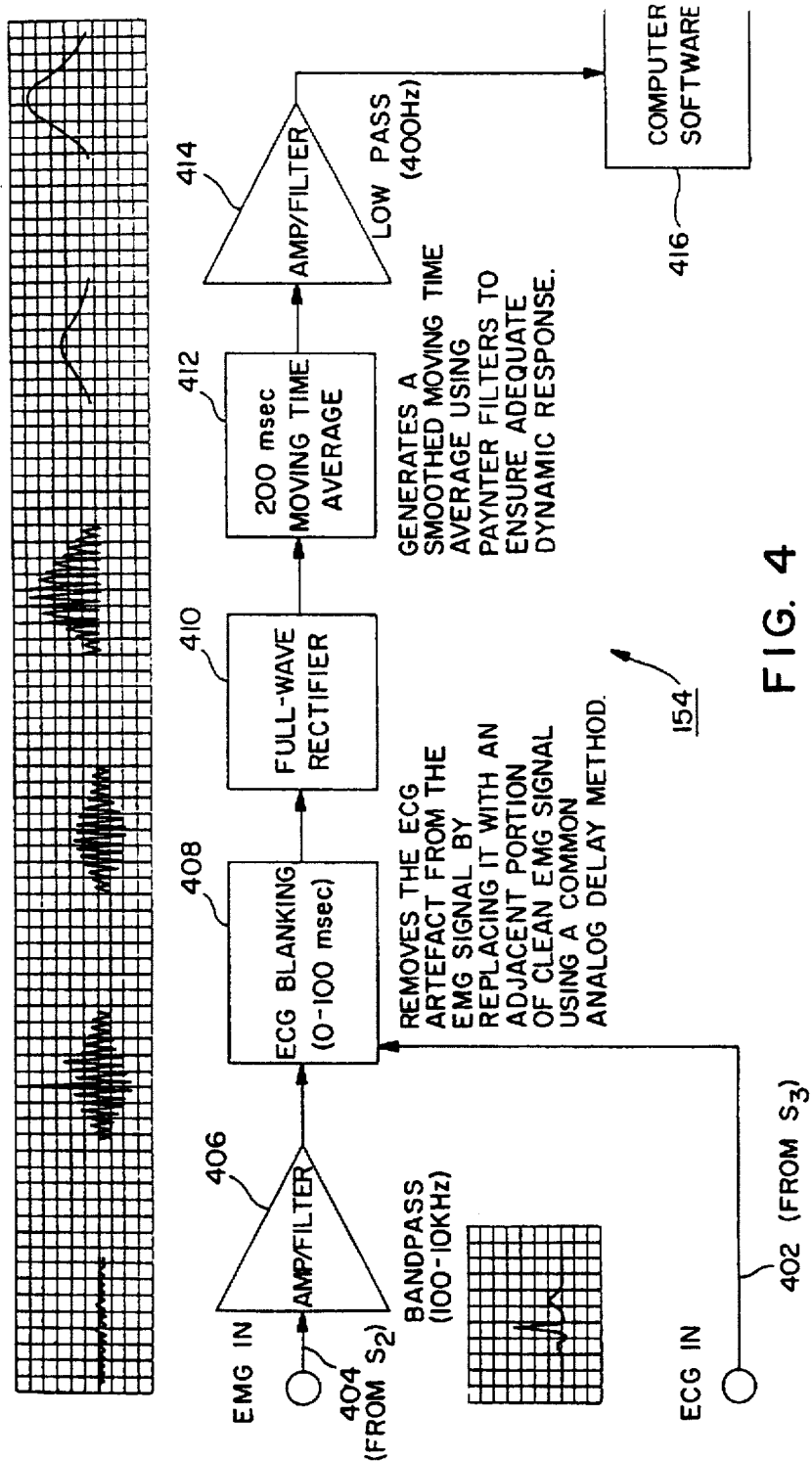
FIG. 4 is a general schematic diagram of the components of the EMG signal processing circuit in FIG. 1.

The preferred embodiments of the present invention include the FIG. 1 block diagram and the FIG. 9–12 physical embodiments of a rate responsive pacing system employing the EMG signal processing described in conjunction with FIGS. 2–4, all taken in connection with the test set up and experimental results described in conjunction with FIGS. 2–6 and Tables 1–17 and the human physiology described in conjunction with FIGS. 7A–7C and 8.

FIG. 1 depicts a block diagram illustrating a rate responsive, demand bradycardia pacemaker incorporating the concepts of the present invention. In the preferred embodiment of FIG. 1, the pacemaker circuit 100 is schematically shown electrically coupled via a pacing lead 102 to a patient's heart 104. Lead 102 includes bipolar electrodes 103 and 105 at the distal end of lead 102 and positioned within the right ventricle (RV) of the patient's heart 104. Lead 102 can carry either unipolar or bipolar electrodes as is well known in the art. In the preferred embodiment, the lead 102 which couples pacemaker to the ventricular endocardium comprises a steroid-tipped electrode, bipolar lead. Electrodes 103 and 105 are coupled via suitable lead conductors through output capacitor 108 to node 110 and to input/output terminals of an input/output circuit block 112.

The input/output circuit 112 contains the operating input and output analog circuits for a digital controlling and timing (digital controller/timer) circuit 132 necessary for the detection of electrical signals derived from the heart, such as the R-wave and the intracardiac EGM (via an EGM amplifier 148), as well as for the application of stimulating pulses to the heart to control its rate under the control of software-implemented algorithms in a microcomputer circuit 114 and control and data signals traversing data buses 130 and 131.

Microcomputer circuit 114 comprises an on-board circuit 116 and an off-board circuit 118. On-board circuit 116 includes a microprocessor 120, a system clock 122, and on-board RAM 124 and ROM 126. Off-board circuit 118 includes an off-board RAM/ROM Unit 128. Microcomputer circuit 114 is coupled by data communication bus 130 to the digital controller/timer circuit 132. Microcomputer circuit 114 may be fabricated of custom IC devices augmented by standard RAM/ROM components. It will be understood by those skilled in the art that the electrical components represented in FIG. 1 are powered by an appropriate implantable-grade battery power source (not shown).

An antenna 134 is connected to input/output circuit 112 for purposes of uplink/downlink telemetry through an RF transmitter/receiver circuit (RF TX/RX) shown at 136. Telemetering both analog and digital data between antenna 134 and an external device, such as an external programmer (not shown), is accomplished in the preferred embodiment by means of all data first being digitally encoded and then pulse position modulated on a damped RF carrier, as substantially described in co-pending U.S. patent application Serial No. 07/468,407, filed Jan. 22, 1990, and assigned to the assignee of the present invention.

A crystal oscillator circuit 138, typically a 32,768 Hz crystal-controlled oscillator, provides main timing clock signals to digital controller/timer circuit 132. A Vref/bias circuit 140 generates a stable voltage reference and bias currents for the analog circuits of input/output circuit 112. An analog-to-digital (ADC)/multiplexer circuit (ADC/MUX) 142 digitizes analog signals and voltages to provide telemetry and replacement time indicating function (EOL). A power- on-reset circuit (POR) 144 functions as a means to reset circuit and related functions to a default condition upon detection of a low battery condition, which will occur upon initial device power-up or transiently occur in the presence of electromagnetic interference, for example.

The operating commands for controlling the timing of the pacemaker depicted in FIG. 1 are coupled by bus 130 to digital controller/timer circuit 132 wherein digital timers set the overall escape interval of the pacemaker, as well as various refractory, blanking and other timing windows for controlling the operation of the peripheral components within input/output circuit 112. In the context of the present invention, the EMG signal picked up from the EMG electrodes (and processed in block 154) is mathematically processed in circuit 114 to develop the current escape interval.

Digital controller/timer circuit 132 is coupled to a sense amplifier (SENSE) 146 for receiving amplified and processed signals picked up from electrodes 103 and 105 through lead 102 and capacitor 108 representative of the near-field electrical activity of the patient's heart 104. SENSE amplifier 146 produces a ventricular sense (VS) event signal for re-setting the escape interval timer within circuit 132. An output pulse generator 150 provides the pacing stimulus to the patient's heart 104 in response to a (VP) trigger signal developed by digital controller/timer circuit 132 each time the escape interval times out, or an externally transmitted pacing command has been received, or in response to other stored commands as is well known in the pacing art.

In an embodiment employing more than one physiologic sensor, e.g., the system disclosed in commonly assigned co-pending U.S. patent application Ser. No. 567,476, filed Aug. 14, 1990 in the name of Bennett et al., digital controller/timer circuit 132 may be coupled to a processing/amplifying circuit (ACTIVITY) 152 for receiving amplified and processed sensor output (Output$_{act}$) from sensor $S_1$ and associated ACTIVITY circuitry which is representative of activity. In a preferred embodiment of the present invention, pacemaker 100 is capable of operating in various non-rate-responsive modes which include VVI, VOO, and VVT, as well as corresponding rate responsive modes of VVIR, VOOR, and VVTR, or may be configured as a dual chamber DDD/DDR pacing system, in certain embodiments described hereafter. A further example of circuitry suitable for implementing this portion of the pacer can be found in U.S. Pat. Nos. 4,596,251 and 4,253,466, which are incorporated herein by reference.

The block diagram of FIG. 1 further includes the EMG signal processing circuit 154 of the present invention for developing a V—V escape interval value to which the V—V escape interval timer circuit is correlated as a function of the patient's minute ventilation as evidenced by the aforementioned measured characteristics of the moving time average EMG signal. The EMG signal processing circuit 154 picks up the raw EMG signal across bipolar electrodes 160, 162 (also depicted in FIG. 1 as the second sensor $S_2$) placed in or near the respiratory muscle as shown for example, as the raw EMG parasternal signal depicted in FIG. 2 and converts that signal into the moving time average EMG parasternal signal depicted also in FIG. 2. The moving time average EMG parasternal signal of FIG. 2 is processed within blocks 132 and 114 to detect the average slope, the maximum slope, the peak, the inspiratory time and the expiratory time all depicted in FIG. 3 to develop the pacing rate control signal as a function of the patient's minute ventilation.

As shown in FIG. 1, the ECG is input to the circuit 100 at the third sensor $S_3$, and then amplified by an amplifier 156 before being input to the EMG signal processing circuit 154.

The details of the EMG signal processing circuit 154 (which was used in the animal experiments described hereafter) will now be described with reference to FIG. 4. The raw EMG signal received from the bipolar electrodes 160 and 162 is input via an input line 404 to a preamplifier/prefilter section 406 for preamplifying and bandpass filtering the EMG signal. The pre-amplification and bandpass filtering are repeated before the processed EMG signal is input to an ECG blanking section 408, which ECG blanking section also receives the ECG signal via input line 402. The ECG blanking section 408 operates to prevent VS and VP signals in the ECG from being passed to a full-wave rectifier 410 for a predetermined blanking period (e.g., between 0 and 100 msec) so that the VS or VP signal does not influence the signal processing of the EMG. The ECG blanking section 408 removes the ECG artifact from the EMG signal by replacing it with an adjacent portion of the clean EMG signal, which does not contain ECG, using an analog delay method known in the art.

The full-wave rectifier 410 full-wave rectifies the EMG signal before passing it to a moving time average section 412, which generates a smooth moving time average using Paynter filters, for example, to ensure adequate dynamic response. The moving time average calculated by the moving time average section 412 is amplified and low-pass filtered by an amplifier/filter section 414, which removes frequency components greater than 100 Hz in the preferred embodiment. The amplified and filtered moving time average signal is further processed by software represented by the block 416 in order to develop a pacing escape interval control signal value for controlling the duration of the pacing escape interval. Recall that the system 100 novelly combines the derivation of rate-influencing minute ventilation from EMG moving time averages with a rate-adaptive demand pacemaker.

Figure 4A:
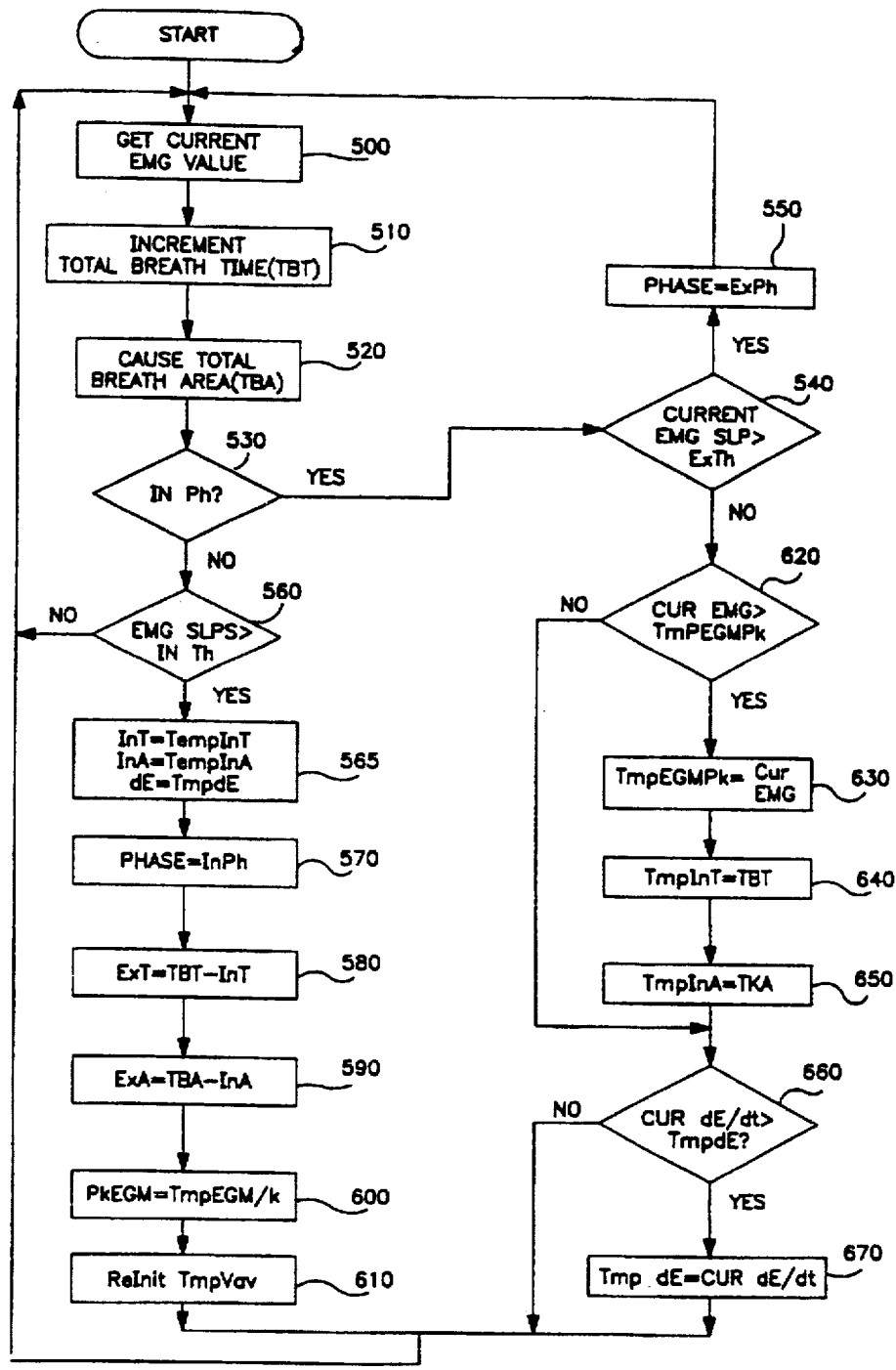
FIG. 4A is a flow diagram of the method/subroutine for processing the EMG signal.

The operation of the software 416 for developing the pacing escape interval control signal value, and hence the pacing escape interval in response to minute ventilation changes will now be described with reference to the flow diagram in FIG. 4A. At the start of the subroutine (Step 500) the microprocessor 120 obtains a new digitized EGM value via the EGM amplifier 148, the ADC/MUX 142, and the digital controller/timer circuit 132. A total breath timer (TBT) is incremented by one sample interval, or 5 msec in the preferred embodiment (Step 510). A total breath area (TBA) is updated by adding the current EMG value to the prior TBA (Step 520).

At Step 530 a determination is made as to whether the patient is in the inspiratory phase (IN Phase) of respiration by an examination of a phase label (PHLab) flag. If the PHLab flag indicates the inspiratory phase (InPh) the program goes to Step 540. Otherwise, the program proceeds to Step 560.

At Step 540 the current EMG slope value (EMGSlp) is examined to determine if it exceeds an expiratory threshold (ExTh) level. If the threshold ExTh is exceeded, the beginning of the expiratory phase EX Phase is indicated, and the program goes to Step 550, which performs no further computations. The program is then returned to the starting point.

If the expiratory threshold level ExTh is not exceeded the program goes to Step 620, where the current EMG (CurEMG) value is compared to a temporary peak value of the EMG (TmpEMGPk). If the CurEMG exceeds the TmpEMGPk, the program goes to Step 630. Otherwise, the program jumps to Step 660 described infra. At Steps 630, 640 and 650 TmpEMGPk is set to equal CurEGM, a temporary inspiratory time (TmpInT) is set to equal TBT, and a temporary inspiratory area (TmpInA) is set to equal TBA, respectively.

The current slope of the EMG (dE/dt) is compared to a temporary value of the slope of the EMG (TmpdE) at Step 660. If dE/dt is less than or equal to TmpdE, the program returns to the beginning Step 500. Otherwise, TmpdE is set to equal dE/dt (Step 670), and the program returns to Step 500.

Returning to Step 530, if the patient is not in the inspiratory phase, IN Phase, as indicated by the PHLab flag, the program moves to Step 560, where the current EMG slope EMGSlp is compared to the inspiratory threshold InTh. If EMGSlp is greater than InTh, the inspiratory time InT is set equal to TmpInT, the inspiratory area InA is set equal to TmpInA, and dE/dt is set equal to TmpdE (Step 565), as the final values of the expiratory phase of respiration, which final values are stored in the microcomputer memory area 124 of the pacemaker 100 in FIG. 1. If EMGSlp is less than or equal to InTh, no further computations are made, and the program reverts to Step 500.

After Step 565 PHLab is set to the inspiratory phase state InPh (Step 570), indicating that the patient is entering the inspiratory phase of respiration. The following then occurs: the expiratory time ExT of the breath just ending is set to equal TBT minus InT (TBT−InT) at Step 580; the expiratory area ExA of the breath just ending is set equal to TBA minus InA (TBA−InA) at Step 590; and the peak value of the EMG (EMGPk) for the breath just ending is set equal to TmpEMGPk (Step 600). Then, all temporary values related to the breath just ending are cleared from their associated program variables (or reset), in order for the program to process information from the next breath. Afterwards, the program returns to the beginning Step 500.

Specific circuitry for the signal processing block/steps of FIGS. 4 and 4A suitable for external experimental verification of the concepts of the present invention is set forth in the following description of the animal experiments and results. It will be understood that the multiple amplification and filtering steps described above may be consolidated into a single bandpass amplifier. For an implantable pacing system, the circuitry may be derived from the above referenced '423 patent, incorporated herein by reference, in conjunction with the specification of parameters set forth in FIG. 4A. The signal processing software may employ the bandpass filtered EMG related signal in algorithms of the type described in the aforementioned commonly assigned U.S. patent application Ser. No. 567,476, which specifies both fixed and programmable signal processing values which affect the sensitivity of the pacing rate change to the magnitude of the EMG related signal over a range of pacing rates. The degree of change in the pacing rate may also be dependent on the then prevailing pacing rate in the range between the programmed lower and upper pacing rate limits.

Experimental Studies and Results

The concept of deriving a minute ventilation related rate control pacing system from EMG signals picked up and processed as described above was explored in a series of dog studies conducted at the Medtronic, Inc. Physiological Research Laboratories. The following Tables 1–17 set forth the data collected as discussed in the following description:

TABLE 1

| Dog Number | Sex | Weight (kg) | Implantations | Studied State |
|---|---|---|---|---|
| 4707 | Female | 24.0 | Parasternal | Anesthetized |
| 4711 | Female | 26.0 | Parasternal | Anesthetized |
| 4684 | Male | 23.6 | Parasternal | Conscious |
| 4833 | Female | 29.6 | Parasternal Azygous | Conscious |
| 4848 | Male | 21.5 | Parasternal Diaphragm | Conscious |

TABLE 2

Steady-State Respiratory Measurements For The Parasternal Intercostal Muscle Experiments Determined By The Pneumotachographic System.

|  | AIR | 4% $CO_2$ | 6% $CO_2$ | 8% $CO_2$ |
|---|---|---|---|---|
| Inspiratory Time | 1.28 | 1.25 | 1.07 | 1.20 |
| (sec) | 0.56 | 0.49 | 0.48 | 0.57 |
| Expiratory Time | 5.49 | 3.85 | 2.61 | 3.38 |
| (sec) | 5.34 | 3.60 | 3.04 | 3.98 |
| Total Breath Time | 6.78 | 5.09 | 3.68 | 4.59 |
| (sec) | 5.89 | 4.08 | 3.43 | 4.53 |
| Respiratory Frequency | 13.51 | 16.08 | 29.07 | 24.54 |
| (breaths/min) | 6.28 | 7.18 | 20.42 | 18.51 |

TABLE 2-continued

Steady-State Respiratory Measurements For The
Parasternal Intercostal Muscle Experiments
Determined By The Pneumotachographic System.

|  | AIR | 4% CO$_2$ | 6% CO$_2$ | 8% CO$_2$ |
|---|---|---|---|---|
| Inspiratory Tidal Volume | 0.81 | 1.07 | 1.27 | 1.45 |
| (liters) | 0.55 | 0.63 | 0.52 | 0.56 |
| Expiratory Tidal Volume | 1.60 | 1.52 | 1.55 | 1.82 |
| (liters) | 1.43 | 0.90 | 0.67 | 0.75 |
| Minute Ventilation | 16.80 | 20.46 | 39.39 | 40.65 |
| (liters/min) | 7.89 | 4.96 | 23.78 | 32.07 |
| Number of Animals | 5 | 4 | 5 | 3 |

Values are means±standard deviations.

TABLE 3

Steady-State Respiratory Timing Measurements
Determined By The Electromyographic System From The
Parasternal Intercostal Muscle.

|  | AIR | 4% CO$_2$ | 6% CO$_2$ | 8% CO$_2$ |
|---|---|---|---|---|
| Inspiratory Time | 0.65 | 0.74 | 0.69 | 0.72 |
| (sec) | 0.27 | 0.47 | 0.57 | 0.39 |
| Expiratory Time | 6.29 | 4.53 | 3.02 | 3.61 |
| (sec) | 5.73 | 4.51 | 3.02 | 3.95 |
| Total Breath Time | 6.94 | 5.27 | 3.71 | 4.32 |
| (sec) | 5.94 | 4.93 | 3.57 | 4.33 |
| Respiratory Frequency | 13.57 | 17.29 | 27.59 | 27.15 |
| (breaths/min) | 6.70 | 8.47 | 16.96 | 19.99 |
| Number of Animals | 5 | 4 | 5 | 3 |

Values are means±standard deviations.

TABLE 4

Correlations Of The Steady-State Responses To
Carbon Dioxide Inhalation Between The Pneumotachographic And
The Electromyographic Timing And Volume Measurements From The
Parasternal Intercostal Muscle Experiments.

|  | Mean Correlation Coefficient | Standard Deviation | Maximum | Minimum |
|---|---|---|---|---|
| Inspiratory Time | 0.29 | 0.23 | 0.57 | 0.01 |
| Expiratory Time | 0.97 | 0.03 | 0.99 | 0.93 |
| Total Breath Time | 0.97 | 0.04 | 0.99 | 0.90 |
| Respiratory Frequency | 0.99 | 0.01 | 0.99 | 0.98 |
| Inspiratory Area | 0.87 | 0.09 | 0.99 | 0.78 |
| Expiratory Area | 0.74 | 0.37 | 0.99 | 0.10 |

Number of animals is 5.

TABLE 5

Correlations Of The Steady-State Responses To Carbon
Dioxide Inhalation Between The Pneumotachographic Minute
Ventilation And The Electromyographic Timing And Effort
Measurements And Indices From The Parasternal Intercostal Muscle.

|  | Mean Correlation Coefficient | Standard Deviation | Maximum | Minimum |
|---|---|---|---|---|
| Inspiratory Time (sec) | 0.41 | 0.28 | 0.73 | 0.03 |
| Expiratory Time (sec) | 0.79 | 0.26 | 0.96 | 0.36 |
| Total Breath Time (sec) | 0.78 | 0.28 | 0.97 | 0.30 |
| Inspiratory Area (volt-sec) | 0.75 | 0.25 | 0.98 | 0.39 |
| Expiratory Area (volt-sec) | 0.91 | 0.04 | 0.97 | 0.85 |
| Delta (volts) | 0.83 | 0.17 | 0.99 | 0.58 |
| Average Slope (volts/sec) | 0.81 | 0.24 | 0.99 | 0.42 |
| Maximal Slope (volts/sec) | 0.88 | 0.13 | 0.99 | 0.71 |
| MV Delta (volts/sec) | 0.98 | 0.02 | 0.99 | 0.94 |
| MV Average slope (volts/sec$^2$) | 0.94 | 0.06 | 0.99 | 0.87 |
| MV Maximal Slope (volts/sec$^2$) | 0.97 | 0.05 | 0.99 | 0.88 |

Number of animals is 5.

TABLE 6

Correlations Of The Transient Responses To Carbon
Dioxide Inhalation Between The Pneumotachographic
And The Electromyographic Timing And Volume
Measurements From The Parasternal Intercostal
Muscle Experiments.

|  | Mean Correlation Coefficient | Standard Deviation | Maximum | Minimum |
|---|---|---|---|---|
| Inspiratory Time | 0.42 | 0.08 | 0.50 | 0.29 |
| Expiratory Time | 0.83 | 0.11 | 0.96 | 0.66 |
| Total Breath Time | 0.81 | 0.14 | 0.97 | 0.62 |
| Inspiratory Area | 0.61 | 0.13 | 0.75 | 0.46 |
| Number of Breaths | 54 | 14 | 71 | 33 |

Number of animals is 4.

Number of transient observations per animal is 3 or 4.

TABLE 7

Correlations Of The Transient Responses To Carbon
Dioxide Inhalation Between The Pneumotachographic Minute
Ventilation And The electromyographic Effort Measurements
And Indices From The Parasternal Intercostal Muscle.

|  | Mean Correlation Coefficient | Standard Deviation | Maximum | Minimum |
|---|---|---|---|---|
| Delta (volts) | 0.70 | 0.08 | 0.82 | 0.59 |
| Average Slope (volts/sec) | 0.69 | 0.16 | 0.85 | 0.48 |
| Maximal Slope (volts/sec) | 0.78 | 0.11 | 0.91 | 0.65 |
| MV Delta (volts/sec) | 0.83 | 0.11 | 0.93 | 0.64 |
| MV Average Slope (volts/sec$^2$) | 0.78 | 0.09 | 0.87 | 0.62 |
| MV Maximal Slope (volts/sec$^2$) | 0.85 | 0.09 | 0.92 | 0.69 |
| Number of Breaths | 54 | 17 | 71 | 33 |

Number of animals is 4.

Number of transient observations per animal is 3 or 4.

TABLE 8

Steady-State Respiratory Measurements For The Diaphragmatic Experiment Determined By The Pneumotachographic System.

|  | AIR | 6% $CO_2$ |
|---|---|---|
| Inspiratory Time | 0.79 | 0.89 |
| (sec) | 0.15 | 0.05 |
| Expiratory Time | 3.04 | 1.75 |
| (sec) | 0.93 | 0.42 |
| Total Breath Time | 3.83 | 2.64 |
| (sec) | 1.08 | 0.47 |
| Respiratory Frequency | 16.39 | 22.73 |
| (breaths/min) | 3.44 |  |
| Inspiratory Tidal Volume | 0.38 | 0.64 |
| (liters) | 0.12 | 0.05 |
| Expiratory Tidal Volume | 0.69 | 0.87 |
| (liters) | 0.15 | 0.06 |
| Minute Ventilation | 11.96 | 20.23 |
| (liters/min) | 3.26 | 2.64 |

Values are means±standard deviations.

TABLE 9

Steady-State Respiratory Measurements Determined By The Electromyographic System From The Diaphragmatic Experiment.

|  | AIR | 6% $CO_2$ |
|---|---|---|
| Inspiratory Time | 0.50 | 0.50 |
| (sec) | 0.35 | 0.25 |
| Expiratory Time | 2.35 | 1.71 |
| (sec) | 1.60 | 0.79 |
| Total Breath Time | 2.85 | 2.21 |
| (sec) | 1.60 | 0.82 |
| Respiratory Frequency | 21.62 | 27.15 |
| (breaths/min) | 3.57 |  |

Values are means±standard deviations.

TABLE 10

Correlations Of The Steady-State Responses To Carbon Dioxide Inhalation Between The Pneumotachographic And The Electromyographic Timing And Volume Measurements From The Diaphragmatic Experiment.

|  | Correlation Coefficient |
|---|---|
| Inspiratory Time | 0.77 |
| Expiratory Time | 0.99 |
| Total Breath Time | 0.99 |
| Respiratory Frequency | 0.99 |
| Inspiratory Area | 0.82 |
| Expiratory Area | 0.32 |

TABLE 11

Correlations Of The Steady-State Responses To Carbon Dioxide Inhalation Between The Pneumotachographic Minute Ventilation And The Electromyographic Timing And Effort Measurements And Indices From The Diaphragm.

|  | Correlation Coefficient |
|---|---|
| Inspiratory Time (sec) | 0.46 |
| Expiratory Time (sec) | 0.94 |
| Total Breath Time (sec) | 0.92 |
| Inspiratory Area (volt-sec) | 0.96 |
| Expiratory Area (volt-sec) | 0.89 |
| Delta (volts) | 0.89 |
| Average Slope (volts/sec) | 0.97 |
| Maximal Slope (volts/sec) | 0.99 |
| MV Delta (volts/sec) | 0.95 |
| MV Average Slope (volts/sec$^2$) | 0.69 |
| MV Maximal Slope (volts/sec$^2$) | 0.98 |

TABLE 12

Correlations Of The Transient Responses To Carbon Dioxide Inhalation Between The Pneumotachographic And The Electromyographic Timing And Volume Measurements From The Diaphragm.

|  | Mean Correlation Coefficient | Standard Deviation |
|---|---|---|
| Inspiratory Time | 0.29 | 0.29 |
| Expiratory Time | 0.75 | 0.26 |
| Total Breath Time | 0.67 | 0.32 |
| Inspiratory Area | 0.47 | 0.21 |

Number of transient observations is 2.

TABLE 13

Correlations Of The Transient Responses To Carbon Dioxide Inhalation Between The Pneumotachographic Minute Ventilation And The Electromyographic Effort Measurements And Indices From The Diaphragm.

|  | Mean Correlation Coefficient | Standard Deviation |
|---|---|---|
| Delta (volts) | 0.63 | 0.23 |
| Average Slope (volts/sec) | 0.36 | 0.28 |
| Maximal Slope (volts/sec) | 0.59 | 0.24 |
| MV Delta (volts/sec) | 0.89 | 0.00 |
| MV Average Slope (volts/sec$^2$) | 0.77 | 0.03 |
| MV Maximal Slope (volts/sec$^2$) | 0.89 | 0.00 |
| Number of Breaths | 22 | 6 |

Number of transient observations is 2.

TABLE 14

Steady-State Respiratory Measurements For The Azygous Venous Experiment Determined By The Pneumotachographic System.

|  | AIR | 4% $CO_2$ | 6% $CO_2$ |
|---|---|---|---|
| Inspiratory Time | 0.92 | 1.29 | 0.81 |
| (sec) | 0.25 | 0.30 | 0.18 |
| Expiratory Time | 2.92 | 3.25 | 1.19 |
| (sec) | 0.86 | 0.54 | 0.34 |
| Total Breath Time | 3.84 | 4.54 | 2.00 |
| (sec) | 1.11 | 0.83 | 0.52 |
| Respiratory Frequency | 15.73 | 13.22 | 30.00 |
| (breaths/min) | 1.26 |  |  |
| Inspiratory Tidal Volume | 0.38 | 0.66 | 0.92 |
| (liters) | 0.18 | 0.21 | 0.27 |
| Expiratory Tidal Volume | 0.65 | 1.00 | 1.16 |
| (liters) | 0.22 | 0.21 | 0.30 |
| Minute Ventilation | 10.60 | 13.45 | 35.21 |
| (liters/min) | 4.01 | 2.54 | 11.30 |

Values are means±standard deviations.

TABLE 15

Steady-State Respiratory Timing Measurements Determined By the Electromyographic System From The Intercostal Muscles Observed From The Azygous Vein.

|  | AIR | 4% $CO_2$ | 6% $CO_2$ |
|---|---|---|---|
| Inspiratory Time | 0.51 | 1.03 | 0.35 |
| (sec) | 0.39 | 0.85 | 0.22 |
| Expiratory Time | 2.67 | 2.54 | 1.28 |
| (sec) | 1.22 | 1.20 | 0.68 |
| Total Breath Time | 3.65 | 3.57 | 1.63 |
| (sec) | 1.97 | 1.54 | 0.69 |
| Respiratory Frequency | 16.65 | 16.81 | 36.81 |
| (breaths/min) | 1.96 |  |  |

Values are means±standard deviations.

TABLE 16

Correlations Of The Steady-State Responses To Carbon Dioxide Inhalation Between The Pneumotachographic And The Electromyographic Timing And Volume Measurements From The Azygous Venous Experiment.

|  | Correlation Coefficient |
|---|---|
| Inspiratory Time | 0.99 |
| Expiratory Time | 0.70 |
| Total Breath Time | 0.79 |
| Respiratory Frequency | 0.94 |
| Inspiratory Area | 0.68 |
| Expiratory Area | 0.87 |

TABLE 17

Correlations Of The Steady-State Responses To Carbon Dioxide Inhalation Between The Pneumotachographic Minute Ventilation And The Electromyographic Timing And Effort Measurements And Indices From The Intercostal Muscles Observed From The Azygous Vein.

|  | Correlation Coefficient |
|---|---|
| Inspiratory Time | 0.46 |
| (sec) |  |
| Expiratory Time | 0.95 |
| (sec) |  |
| Total Breath Time | 0.91 |

TABLE 17-continued

Correlations Of The Steady-State Responses To Carbon Dioxide Inhalation Between The Pneumotachographic Minute Ventilation And The Electromyographic Timing And Effort Measurements And Indices From The Intercostal Muscles Observed From The Azygous Vein.

|  | Correlation Coefficient |
|---|---|
| (sec) |  |
| Inspiratory Area | 0.91 |
| (volt-sec) |  |
| Expiratory Area | 0.83 |
| (volt-sec) |  |
| Delta | 0.19 |
| (volts) |  |
| Average Slope | 0.77 |
| (volts/sec) |  |
| Maximal Slope | 0.37 |
| (volts/sec) |  |
| MV Delta | 0.63 |
| (volts/sec) |  |
| MV Average Slope | 0.86 |
| (volts/sec$^2$) |  |
| MV Maximal Slope | 0.83 |
| (volts/sec$^2$) |  |

Figure 5:
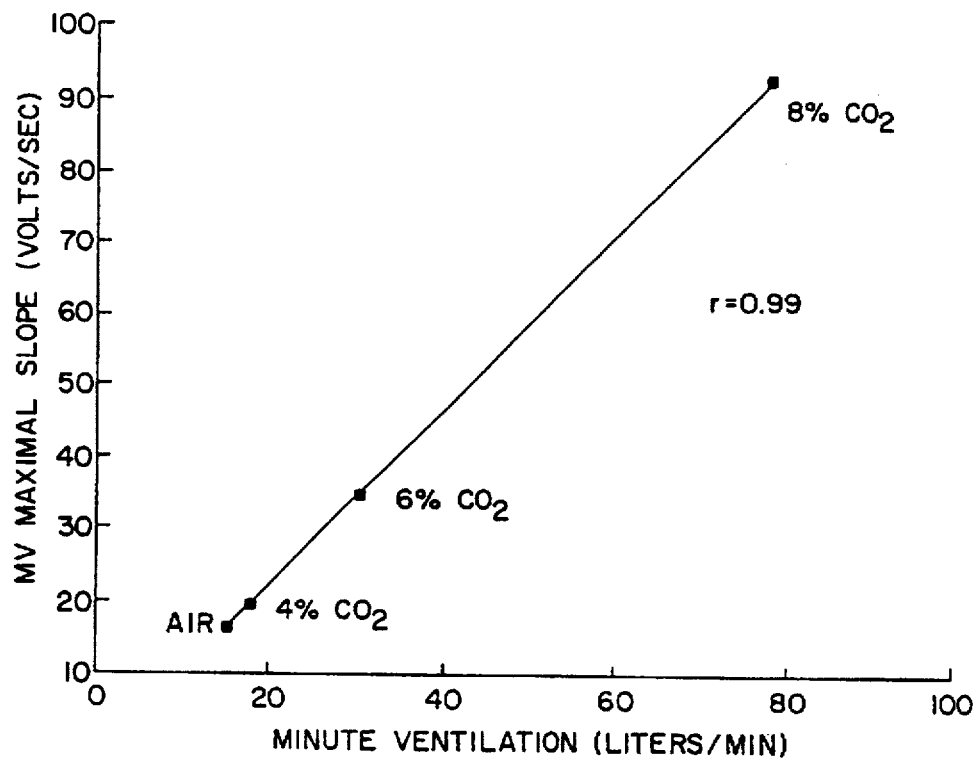
FIG. 5 is a graph of the steady state response to carbon dioxide inhalation in a dog: minute ventilation versus maximal slope.
Figure 6:
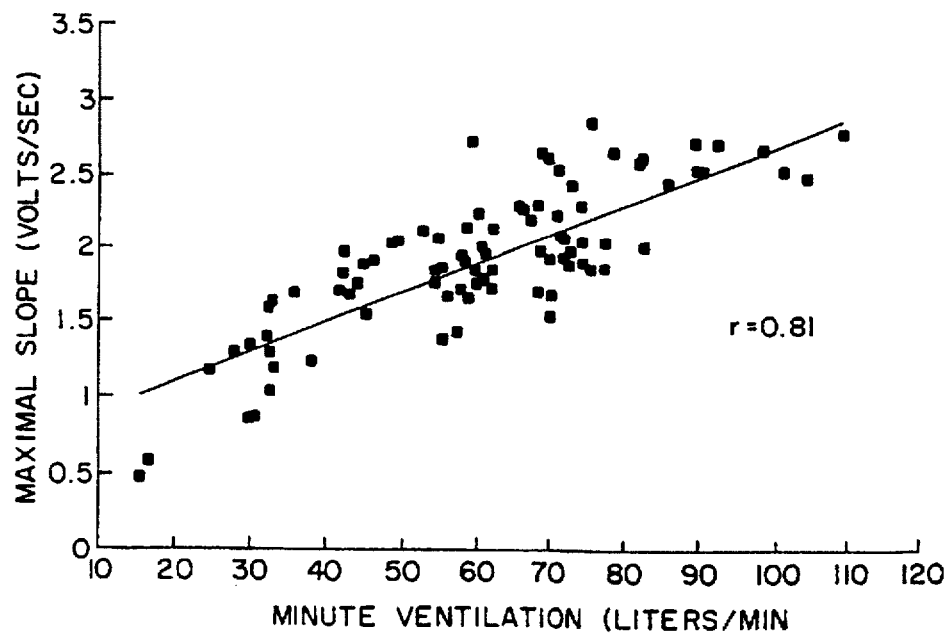
FIG. 6 is a graph of a transient response to carbon dioxide inhalation in a dog: minute ventilation versus maximal slope.

Turning now to FIGS. 5 and 6, the data derived from dog testing of a single dog depicts the correlation of the maximal slope in volts per second to the concurrently measured minute ventilation in liters per minute over a range of values of carbon dioxide in the air breathed by the dog in testing. The maximal slope correlates highly to the minute ventilation and forms one basis for the algorithm of the present invention.

In experimental animal studies undertaken to show concept feasibility, five dogs had surgically formed chronic tracheostomies for the measurement of the actual minute ventilation by means of a standard pneumotachography system. The animals were also chronically implanted with custom leads to sense the electromyographic signal from a parasternal intercostal muscle (five dogs), the diaphragm, and a thoracic intercostal muscle (one dog each). These muscles physically contracted only during the inspiratory periods of breathing. This factor allowed for distinguishing one breath from another to calculate the respiratory rate. It also allowed for the calculation of various breath-by-breath tidal volume indices from the electromyographic signals. The product of the respiratory rate and the tidal volume indices would yield several minute ventilation indices. The raw electromyograms were amplified, band-pass filtered (100–3,000 Hz), full-wave rectified, electrocardiogram-blanked, and moving time averaged (200 msec). The moving time averages and pneumotachographic signals were continuously recorded during the inhalation of air (five dogs), and twenty minutes each of gas mixtures containing four (four dogs), six (five dogs), and eight percent (three dogs) carbon dioxide in air. The indices of minute ventilation included: the height of the moving time average signal, the maximal slope of the signal, a two-point average slope of the signal, and each of these divided by the total breath time. Each was obtained on a breath-by-breath basis during the few minutes transition period from the inhalation of air to a gas containing carbon dioxide and back again, and during the stable, steady-state period of each gas inhalation. Correlations were made between the pneumotachographic and electromyographic measures of respiratory rate, and between the actual minute ventilation and each of the electromyographic indices of minute ventilation.

The correlation coefficients of the electromyographically-derived respiratory rate versus the true respiratory rate during the steady-state were 0.97 for the total breath time and 0.99 for the respiratory frequency for the parasternal intercostal muscles, 0.99 and 0.99 for the diaphragm, and 0.79 and 0.94 for the thoracic intercostal muscles. For the transient responses, the correlation coefficients were 0.81 for the total breath time for the parasternal intercostal muscles and 0.67 for the diaphragm. None were performed for the thoracic intercostal muscles. The correlation coefficients of the actual minute ventilation with the six electromyographic minute ventilation indices during the steady-state were between 0.81 and 0.98 for the parasternal intercostal muscles, 0.69 and 0.99 for the diaphragm, and 0.37 and 0.86 for the thoracic intercostal muscles. For the transient responses, the correlation coefficients were between 0.69 and 0.85 for the parasternal intercostal muscles and 0.36 to 0.89 for the diaphragm. For the most part, the highest correlation coefficients occurred for the indices that were normalized for the total breath time.

It was concluded that the utilization of the respiratory muscle electromyogram to assess the minute ventilation is definitely feasible. While the results of this investigation were limited by the number of animals, the measurement sites, and the particular experimental conditions, it was concluded an electromyography-based respiration sensing feature for future rate-responsive pacing may hold promise.

For this investigation, a maximum of three multipolar leads were implanted transvenously, through the jugular vein, and two multipolar leads were implanted by alternate routes. Fluoroscopy was utilized to ensure accurate site locations.

Either a Medtronic Model 4016, 4016A, 4058 bipolar screw-in lead was inserted into the right ventricle, or a custom quadripolar atrial/ventricular screw-in lead was implanted in each dog. In four dogs, a 7F custom quadripolar lead was inserted into the azygous vein and wedged as far distally into that location as possible. Two of the custom leads were made with short tines, while two were made without tines. Each lead had a tip electrode, and the interelectrode distance was 10 mm. Each electrode wire coil from the custom leads was crimp-connected to a temporary heart wire within the body of the lead during the lead manufacturing, only the heart wires were to exit through the animal's skin. The standard bipolar cardiac leads were connected to in-line lead-to-heart wire adapters at the time of the implantation surgery. The site of exit of the heart wires was at the dorsal midline between the shoulders. In addition to the transvenous leads, there were two sites of alternate route lead implantations. In each dog, a Medtronic dual Model 4951 custom bipolar lead was surgically placed over the parasternal intercostal muscle in each dog for electromyographic sensing. Additionally, in one dog the diaphragmatic electromyographic signals were sensed in one dog by direct electrode insertion of a dual Model 4951 custom bipolar lead to the midline costal portion of the muscle following a midline laparotomy. The electrodes for both the parasternal and electromyographic leads were inserted into the muscles parallel to the muscle fascicles. As with the transvenous leads, the electrode wires of these leads were also crimp-connected to the same temporary heart wires within the lead body during their manufacturing. The heart wires exited through the animal's skin at the same location as the other leads.

The dual Model 4951 leads were of two types—both involved cutting the plastic pads between the electrodes, then gluing the two, to have a side-by-side interelectrode distance of 3 mm. This was all to be done for the first type. In the second type, the barbed portion of the electrodes were altered by bending the electrode down to become perpendicular to the urethane pad, then cutting the electrode to either 3 or 6 mm in length. The first type was utilized for the diaphragm and one parasternal intercostal site, while the second type was implanted in four dogs in the parasternal location. A minimum of three post-operative days were allowed for healing before any study protocol was started.

The experiments were performed with set-up hardware including: a Dell computer and monitor, a TEAC XR-50 14-channel video cassette data recorder, a Grass P 15 AC preamplifier, two Tektronix AM 502 differential amplifiers, an eight-channel Gould electrostatic recording system, a Hans Rudolph 3813 linear pulmonary pneumotachometer with a Validyne DP45 differential pressure transducer and CD23 carrier demodulator, a Cole-Parmer high flow variable-area air flowmeter, a CWE, Inc. SB-1 EKG blanker and an MA-821/RSP rack-mounted moving averager. The tape and chart recorded channels were: ventricular electrogram, airflow, one of the various raw electromyograms, and the full-wave rectified moving time averaged electromyogram.

Because the electromyographic signals are typically only microvolts in amplitude, the raw respiratory signals usually contain higher amplitude interference signals from the cardiac electrical activity, the electrocardiogram. To eliminate this, most investigators have utilized high-pass frequency filtration of over 50 to 100 Hz to hopefully eliminate most of this interference without compromising the quality of the desired electromyographic signal components. Complete electrocardiographic signal elimination does not take place, while some of the electromyogram is lost. Other investigators have developed blanking or gating circuits to detect and eliminate the electrocardiographic components from the electromyographic signal. In these studies, a combination of band-pass frequency filtration of from 100 to 3,000 Hz, with a Grass P 15 AC preamplifier and a Tektronix AM 502 differential amplifier in series, and a blanking circuit from CWE, Inc. was used. The signal was then full-wave rectified and integrated using third-order Paynter filters, also from CWE, Inc., to produce what is known as a moving time average of the signal with a time constant of 200 msec. A final stage of low-pass filtering from DC to 100 Hz was done with another Tektronix amplifier prior to the computer analysis of the signal. A diagram of the experimental signal acquisition set-up is presented in FIG. 1.

Prior to experimentation, the pneumotachograph was calibrated with a known air flow, usually 50 liters/min, measured from the Cole-Parmer flowmeter. The output from the Validyne carrier demodulator was then set to a desired output voltage, usually 0.5 volts, relating to the selected air flow.

Once the electromyographic signals were confirmed to be present and the electrocardiographic components of the signal were blanked, the endotracheal tube would be inserted into the animal's airway, and it would be connected to the pneumotachograph and gas delivery system. The endotracheal tube was coated with a 1% lidocaine gel to allow for easy passage of the tube into the tracheal opening and to anesthetize any irritability due to the tube. If the animal would not tolerate the endotracheal tube, as indicated by coughing, hacking, excessive breathing, or incessant movements, the dog would be intravenously anesthetized with 30 mg/kg sodium pentobarbital, placed on the left side over a heating blanket to maintain the body temperature, and the experiment would then proceed.

The experimental protocol was as follows:

Control—the inhalation of room air for ten minutes,

Gas 1—the inhalation of a gas containing either four, six, or eight percent carbon dioxide in air for twenty minutes, Control—the inhalation of room air for ten minutes, Gas 2—the inhalation of a different carbon dioxide-containing gas for twenty minutes, Control—the inhalation of air for ten minutes, Gas 3—if tolerated, an inhalation of a third gas containing carbon dioxide for twenty minutes, Control—the inhalation of air for up to ten minutes.

The 4, 6, and 8% carbon dioxide inhalations were typically delivered in a random sequence. Intolerance of the eight percent carbon dioxide gas was indicated by noticeable agitation with severe bodily movements. If this took place, the gas was immediately replaced by air. The twenty-minute time period was selected because physiologically it takes at least six minutes to reach a minute ventilatory steady state in a large mammal, followed by several minutes of data acquired for topics other than those in this report. The objective of the graded-step characteristic of the hypercapnic inhalants was to induce graded increased minute ventilation responses by the animals.

The data analysis utilized breath-by-breath analysis of the cardiac asynchronous respiratory waveforms and storage of derived parameters. The chart recording of the pneumotachographic and the raw and moving time average electromyographic signals are presented in FIG. 2. A signal amplitude threshold scheme was used for the detections on the pneumotachographic signal. The beginning of inspiration was detected by the signal exceeding a preselected negative threshold. Similarly, the beginning of expiration, and the end of inspiration, was detected by the pneumotachographic signal exceeding a preselected positive threshold.

In contrast to the amplitude threshold detection system for the pneumotachographic signal, a slope change detection scheme was used for the electromyographic moving time average.

The beginning of inspiration was detected when the slope of the moving time average exceeded a preselected positive slope value. The end-inspiratory detection, and, in effect, the beginning of expiration, occurred when a negative slope of the signal went below a preselected threshold. The end-expiratory detection was at the point of detection of the beginning of the succeeding breath's detection of inspiration.

These slope threshold detections served the purpose of filtering the lower frequency changes in the electrical baseline due to the artifacts of animal movement.

The computer derived measures of each breath from the pneumotachogram included: inspiratory time, expiratory time, total breath time, inspiratory tidal volume, expiratory tidal volume, and inspiratory-derived and expiratory-derived minute ventilation. The minute ventilation was calculated on a breath-by-breath basis as the product of the tidal volume and the respiratory rate determined from the total breath time.

For the electromyograms, the computer derived measures of the moving time average also included the inspiratory time, the expiratory time, and the total breath time. Other measures included:

Inspiratory area—the area under the curve from threshold positive inspiratory slope voltage to the peak voltage, Expiratory area—the area under the curve from the peak voltage to the next threshold positive inspiratory slope voltage, Delta—the difference between the peak voltage and the threshold positive inspiratory slope voltage, Average Slope—the two-point slope of the moving time average between the threshold positive inspiratory slope voltage and the peak voltage, Maximal Slope—the maximal slope of the inspiratory moving time average, MV Delta—the ratio of the Delta and the total breath time, MV Average Slope—the ratio of the Average Slope and the total breath time, MV Maximal Slope—the ratio of the Maximal Slope and the total breath time.

An illustration of the threshold, timing, and measurement determinations for the moving time average is presented in FIG. 3. Measures for the human diaphragm, similar to the described Delta and Average Slope, have been shown by others to correlate highly with the actual minute ventilation during short-term, transient responses to carbon dioxide rebreathing.

Post-experimental data processing utilized LOTUS 1-2-3.Four-breath moving averages of the pneumotachographic and electromyographic measures and indices were calculated prior to further data analysis. Pearson product-moment correlations were made in each animal for the steady-state and transient responses to the inhaled carbon dioxide. Mean steady-state values for each of the various pneumotachographic and electromyographic determinations were made in each animal at a time when the ventilatory response to each gas had reached a fairly stable value. Using these mean values, correlations were made for each animal over the range of gases between the associated pneumotachographic and electromyographic timing and volume measurements (e.g., inspiratory time determined by pneumotachography versus inspiratory time determined by electromyography). These analyses allowed for the determination of the degree of correlation between the experimentally derived electromyographic values and their standard, reference counterparts measured by the pneumotachographic signals. In addition, the correlations between the minute ventilation determined by pneumotachography and the electromyographic timing and effort measurements and indices (e.g., minute ventilation versus Delta) were performed. Studies were also made of the behavior of the experimental variables during the periods where a ventilatory gas change had been performed, and the animals were in a transition from one respiratory steady-state to another. Several-breath values for each of the various pneumotachographic and electromyographic determinations were made in the animals during these relatively short, transient time periods. Correlations were made for each animal during these transient periods with the same comparisons as the steady-state responses described above. For each animal, average transient correlation coefficients were then calculated.

Two of the five animals would not tolerate the insertion of the endotracheal tube. Only one of the three remaining conscious dogs would tolerate the inhalation of the gas containing eight percent carbon dioxide. Only one of the leads implanted into the azygous vein remained in that site long enough for electromyographic studies to be made. This was one of the two tined leads. Most likely, the high blood flow from that vein and the animals' movements, combined with the great flexibility and small diameter of the leads, lead to their dislodgement. The lead tips moved with the blood flow to end up in the right ventricle. Table 1 lists the Medtronic, Inc. Physiological Research Laboratory identification numbers of the experimental dogs, and the sexes, weights, successful implantations, gases inhaled, and examined state of each.

With the inhalation of gases containing increasing concentrations of carbon dioxide, marked increases in the steady-state actual respiratory frequency, inspiratory tidal volume, and minute ventilation, and decreases in the expiratory time and total time per breath were observed. The inspiratory time and the expiratory tidal volume did not change with the inhalation of carbon dioxide (Table 2). Theoretically, the inspiratory and expiratory tidal volumes should be very close to one another. This was the case for the conscious animals. On a breath by breath basis, the correlation coefficients between the inspiratory and expiratory tidal volumes were 0.99, 0.99, and 0.99. For the two anesthetized dogs, the same comparison yielded correlation coefficients of 0.35 and 0.83. The cause for the differences between the inspiratory and expiratory tidal volume measurements for the conscious and anesthetized animals is unknown, but may have been due to differences in the specific breathing patterns in the two states; differences that underestimated one volume relative to the other under the constraints of the pneumotachographic system and its timing detection schemes. Most references relate the expiratory minute ventilation as the measure for "minute ventilation." Therefore, the correlations between the actual minute ventilation and the electromyographic timing and effort measurements and indices used the pneumotachographic expiratory minute ventilation measurements.

Also with the inhalation of increasing concentrations of carbon dioxide, the electromyographically determined expiratory time and total time per breath progressively decreased as the respiratory frequency increased. The inspiration time did not appear to change (Table 3). When a study was made between the steady-state pneumotachographic and the steady-state electromyographic timing variables, very high correlations were observed for the expiratory time, the total time per breath, and the respiratory frequency. This indicates that the electromyographic system does follow respiratory rate well in the steady-state. Correlations between the "volume" measurements of inspiratory and expiratory areas, liters versus volt-sec. were not quite as high (Table 4).

Correlations were performed in each dog between the steady-state minute ventilations and the electromyographic measurements of breath timing and effort for the various gases. The average correlation coefficients are presented in Table 5. FIG. 5 illustrates a steady-state response to the inhalation of carbon dioxide in an animal. The best correlations with the minute ventilation were for the moving time average Delta and Slope measurements divided by the total breath time; MV Delta, MV Average Slope, and MV Maximal Slope. By itself, the Maximal Slope of the moving time average also correlated very well with the minute ventilation. This indicates that the electromyographic system does follow respiratory effort well in the steady-state.

Correlations were then performed in each dog between the pneumotachographic and the electromyographic timing, volume, and effort measurements and indices for the transient responses to the various carbon dioxide containing gases; air to X % carbon dioxide and X % carbon dioxide to air. A graph of the transient response to the inhalation of 8% carbon dioxide in a dog is presented in FIG. 6. For each animal, its total transient observations were averaged, and the means of the animals are presented in Tables 6 and 7. All of the transient responses were not analyzed in every dog due to several factors: a transient loss at some time of some of the electromyographic signal during the transition period, the tape recorder was turned off at some time during the transition period, no distinguishable transition breathing pattern was discernible, the animal's breathing pattern was too irregular entering into or at the end of the transition period to properly demarcate the transition period, and the number of breaths in the transition period was very small. The transient responses in one anesthetized animal were eliminated due to the first factor. Three of the remaining animals had four transient responses analyzed, while one had three. As with the steady-state periods, good correlations were noted between the pneumotachographic and electromyo-graphic expiratory time and total breath time. Also, as in the steady-state periods, the Maximal Slope of the inspiratory moving time average and the MV Delta, MV Average Slope, and the MV Maximal Slope of the moving time average had good correlations with the actual minute ventilation. These results indicate that the electromyographic system does follow both respiratory rate and effort well not only in the steady-state but during transition periods also.

The six Tables 8 through 13 correspond for the single diaphragmatic electromyographic experiment to the six Tables 2 through 7 for the five parasternal intercostal muscle experiments. All of this animal's steady-state respiratory measurements for air and 6% carbon dioxide inhalation (Table 8) fall within one standard deviation for the group of five animals (Table 2). The same is true for the steady-state respiratory timing measurements determined by the electromyographic system (Tables 3 and 9).

Like the steady-state responses to carbon dioxide inhalation for the parasternal intercostal muscles (Table 4), the respiratory timing measurements of expiratory time, total breath time, and respiratory frequency correlated highly between the pneumotachographic and the electromyographic systems (Table 10). This indicates that, like the parasternal intercostal muscle experiments, the electromyographic system for the diaphragm does follow respiratory rate well during the steady-state.

Correlations of the steady-state responses to carbon dioxide inhalation between the minute ventilation and the electromyographic determinations of expiratory time, total breath time, and inspiratory and expiratory areas were high. Also possessing high correlation coefficients were the relationships between the minute ventilation and the Delta, the Average Slope, the Maximal Slope, the MV Delta, and the MV Maximal Slope (Table 11). Like the parasternal intercostal muscle experiments, this indicates that the electromyographic system for the diaphragm does follow respiratory effort well during the steady-state.

Concerning the transient responses to the initiation and removal of 6% carbon dioxide to the animal instrumented to record the diaphragmatic electromyograms, there were no very good correlations between the pneumotachographic and electromyographic timing and volume measurements (Table 12). While the Delta and Maximal Slope determinations divided by the total breath time did correlate well with the minute ventilation, the correlation coefficient did not exceed 0.90. Reasons for this are the lower numbers of breaths compared to the parasternal intercostal experiments (Table 7) and the fact that only two transient observations were recorded.

Tables 14 through 17 for the recordings of the intercostal muscle experiment correspond to Tables 2 through 5 for the parasternal intercostal muscle experiments and Tables 8 through 11 for the diaphragm experiment. All of this animal's steady-state respiratory measurements for air, 4%, and 6% carbon dioxide inhalation (Table 14) fall within one standard deviation for the group of five animals (Table 2).

The same is true for the steady-state respiratory timing measurements determined by the electromyographic system (Tables 3 and 15).

The lead used to obtain the intercostal muscular electromyograms by way of the azygous vein was a quadripolar lead with an interelectrode distance of 10 mm. Various interelectrode combinations were made to obtain the largest electromyographic signal corresponding to inspiration with the least amount of electrocardiographic or blanking artifacts. The only electrode combination what fulfilled these criteria was electrodes 2 and 4, where electrode 4 was the tip electrode.

Correlations of the steady-state responses to carbon dioxide inhalation between the pneumotachographic measurements and those derived from the electromyographic measurements from the azygous vein are presented in Table 16. High correlations were noted for the inspiratory time, the respiratory frequency, and the expiratory area. Table 17 illustrates the correlation coefficients between the minute ventilation and the electromyographic timing and effort measurements and indices from the inspiratory muscles observed through the azygous vein. Besides the high correlations for the expiratory time, the total breath time, and the inspiratory area, the MV Average Slope correlated very well with the minute ventilation. Many of these and other correlations differed markedly from those observed from the parasternal intercostal muscles and the diaphragm.

The electromyograms for the electrode combination of 2 and 4 of the midthoracic mixed internal/external intercostal muscles were not recorded during the transitions from air to either 4% or 6% carbon dioxide, and vice versa. Therefore, there are no transient electromyographic data to report on this muscle group.

The important considerations when selecting potential muscles for respiratory EMG studies are the type and pattern of their EMG activity. The muscles investigated in this study all possess phasic activity, i.e., all contract during inspiration and are electrically silent during expiration. This phasic property is important for determining the duration of individual breaths, thus, determining the respiration rate. Additionally, the phasic activity allows distinguishing one breath from another to examine the effort characteristics of each breath.

Another valuable advantage of a phasic electromyographic signal for rate-responsive pacing is the lack of need for a comparison to a derived long term baseline. Such a requirement complicates presently available and planned impedance-based respiration devices. In an EMG-based pacemaker, the electrical silence following the inhalation phase of each breath is the baseline.

Still another important consideration for which various EMG's may be of utility for pacing devices is signal accessibility. The parasternal intercostal muscles were also chosen for study because of their close proximity to the potential pacemaker pocket at implant. Therefore, the signals may be accessed with few modifications to the traditional implantation procedures. The external intercostal muscles were additionally chosen because the potential to obtain the electrical activity through an auxiliary transvenous lead—a procedure quite manageable by most pacemaker implanters. In contrast, the diaphragm was also chosen due to its familiarity to physicians as the major muscle of respiration and because it may be accessed from a number of approaches.

It has been reported in the literature, based on transient breathing studies in humans, that measurements similar to the Delta and Average Slope of the diaphragmatic EMG moving time average correlate very well with the actual minute ventilation. This evidence led us to hypothesize that the same should take place in the dog—not only for transients, but for steady-state analyses as well. In addition, we further hypothesized that these correlations should translate across all the other major inspiratory muscles.

In this study, several direct or derived respiratory effort measurements from the EMG's of several inspiratory respiratory muscles did correlate well with the actual minute ventilation under the experimental conditions.

The EMG recorded between a set of bipolar electrodes represents the total electrical activity of a particular region of a muscle group. This electrical activity will later be associated with the mechanical activity of that muscular region. An increased EMG activity of the recorded respiratory muscles involves the recruitment of more motor units during the inhalation period. A motor unit consists of a single nerve coming from the central nervous system and all of the individual muscle fibers it innervates. The amplitude of the moving time average, Delta, may be thought of as an estimate of the total quantity of the motor unit recruited for a given breath. The two slopes of the moving time average would provide estimates of the rate of recruitment of the motor units for that breath. Both the quantity and rate of recruitment of the respiratory muscle motor units are indices of the respiratory effort for a given breath and should be related to the actual breath size or tidal volume of the breath. Dividing these values by the total breath time, which is equivalent to multiplying these values by the respiration rate, provides parallel indices of the actual minute ventilation. Indeed, values for these indices from the parasternal intercostal muscle, the MV Delta, the MV Average Slope, and the MV Maximal Slope, all correlated highly with the actual minute ventilation. These good correlations existed both for the steady-state and the transition periods. Similar results were observed for the diaphragm and, to a lesser degree, for the external intercostal muscles sensed through the azygous vein, although minimal data were available for these. In addition to the good correlations between the indices of respiratory effort and the actual minute ventilation, we also found very good correlations between the total breath time and the respiratory rate derived from the respiratory muscles' EMG's and those obtained from the pneumotachographic signals.

From these results, a practical electromyographic feature system to track the minute ventilation could be envisioned. However, several technical design issues should be considered. First, the characteristics of the EMG's from the three respiratory muscle groups studied varied somewhat to the carbon dioxide stress. This indicates that an EMG-measuring feature in an implantable pulse generator may need to be tailored to the specific target muscle. Second, it may not be practical for the pacemaker to measure the EMG's continuously as was done in this study. Thus, gating the measurement on and off as required to make the measurement of interest may make the energy requirements more practical. One system could use the Maximal Slope of the moving time average. This signal is already an "instantaneous" measure of the slope of the moving time average. This picture assumes no motion artifacts. If motion artifacts are present, the electrical silence may be replaced by small slopes. A slope threshold indicating the beginning of an inhalation would then be necessary. Multiplying the maximal instantaneous slope during the inhalation period by the respiratory frequency, 60 (sec/min)/the breath-to-breath interval (sec), would yield a minute ventilation index. However, not all of the inspiratory muscles' Maximal Slopes of the moving time average worked as well to describe the minute ventilation.

Human Anatomy

Figure 7:
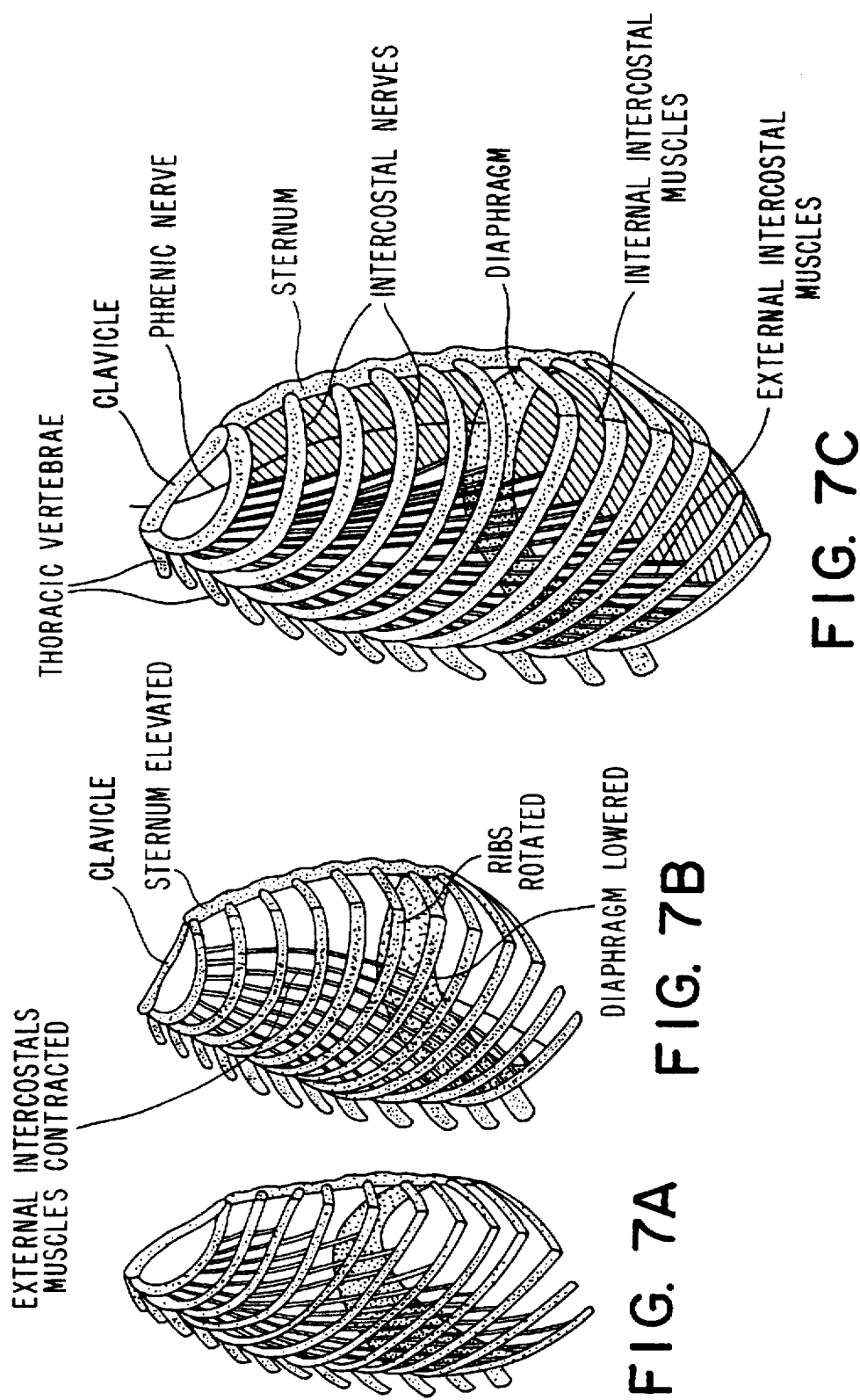
FIG. 7A–7C are depictions of the external and internal intercostal muscles of a human rib cage.

Turning now to FIGS. 7A–7C, three views of the human skeletal thorax including the diaphragm, rib cage, external and internal intercostal muscles during inspiration and expiration are depicted. FIG. 7A depicts the relative orientation of the rib cage, diaphragm and external and intercostal muscles during expiration and in the period between inspiratory events. FIG. 7B depicts the increase in the volume of the thorax during inspiration due mainly to an increase in its vertical dimensions as the contracting diaphragm descends. The antero-posterior dimension of the thorax is increased by the rotation of the ribs caused by the contraction of the external intercostal muscles. Accessory muscles that raise the sternum and clavicle help increase the thoracic size. FIG. 7C depicts the orientation of both the external and internal intercostal muscles as well as the phrenic nerve and diaphragm. The external intercostal muscles elevate the ribs in normal inspiration; relaxation of these muscles causes expiration, as the ribs descend. Internal intercostal muscles are active only in forced expiration or very deep breathing.

The diaphragm is the most important of the respiratory muscles. It is a thin, movable partition between the thorax and the abdomen, forming a vaulted roof to the abdomen. The diaphragm is higher on the right than on the left. The central part is a very strong tendon that is attached to the margins of the outlet from the thorax. The muscular part forms a dome-shaped structure originating on the ribs and sternum or on the upper lumbar vertebrae posteriorly. The diaphragm has three large apertures and several smaller ones through which pass the aorta, the esophagus, and the inferior vena cava.

Contraction of the diaphragm increases the size of the thoracic cavity in three diameters, but chiefly by lengthening its vertical diameter as the diaphragm descends as depicted from FIG. 7A to FIG. 7B. The diaphragm is the main muscle of inspiration. When it relaxes, passive expiration results, which is sufficient for quiet breathing.

The external intercostal muscles are mainly responsible for the elevation of the ribs in normal, quiet breathing. They are inserted between two neighboring ribs, sloping forward and downward as depicted in FIG. 7C. Relaxation of these muscles brings about passive expiration.

The internal intercostal muscles form a deeper layer of muscle tissue between the ribs with the fibers running in the opposite direction, from above, downward and backward. On contraction, these muscles depress the ribs, aiding in expiration during forced or very deep breathing. This is active or forced expiration.

The increase in the size of a thoracic cavity affects the pleural pressure in the cavity outside the lungs which was measured by Funke through the use of a pressure transducer in the pleural cavity and relied upon by Nappholz in the measure of blood impedance within the great veins and the heart. All of the techniques employing impedance plethysmography rely upon the expansion and contraction of the volume within the rib cage to develop the signals representative of respiratory rate and/or minute volume.

The physiological responses of the electrical activity of respiratory muscles have been widely studied by a large number of researchers. All of the respiratory muscles, in addition to those specifically described above, have been studied to some extent. While all have a role in the activity of breathing, some increase their activities during exertion, while several normally significantly contribute to posture. Such muscles with multiple activities are not suitable for developing the EMG signal leaving the external, parasternal, and internal intercostal muscles, the scalenes, the sternocleidomastoid, and the diaphragm as primary candidates for development of pacing rate control signals.

The important considerations when selecting potential muscles for respiratory EMG studies are the type and pattern of their EMG activity. The muscles investigated in this study act as spacing activity; all contract during inspiration and are electrically silent during expiration. This phasic property is important for determining the duration of individual press, thus determining the respiration rate. Additionally, the phasic activity allows distinguishing one breath from another to examine the effort characteristic of each breath.

Figure 8:
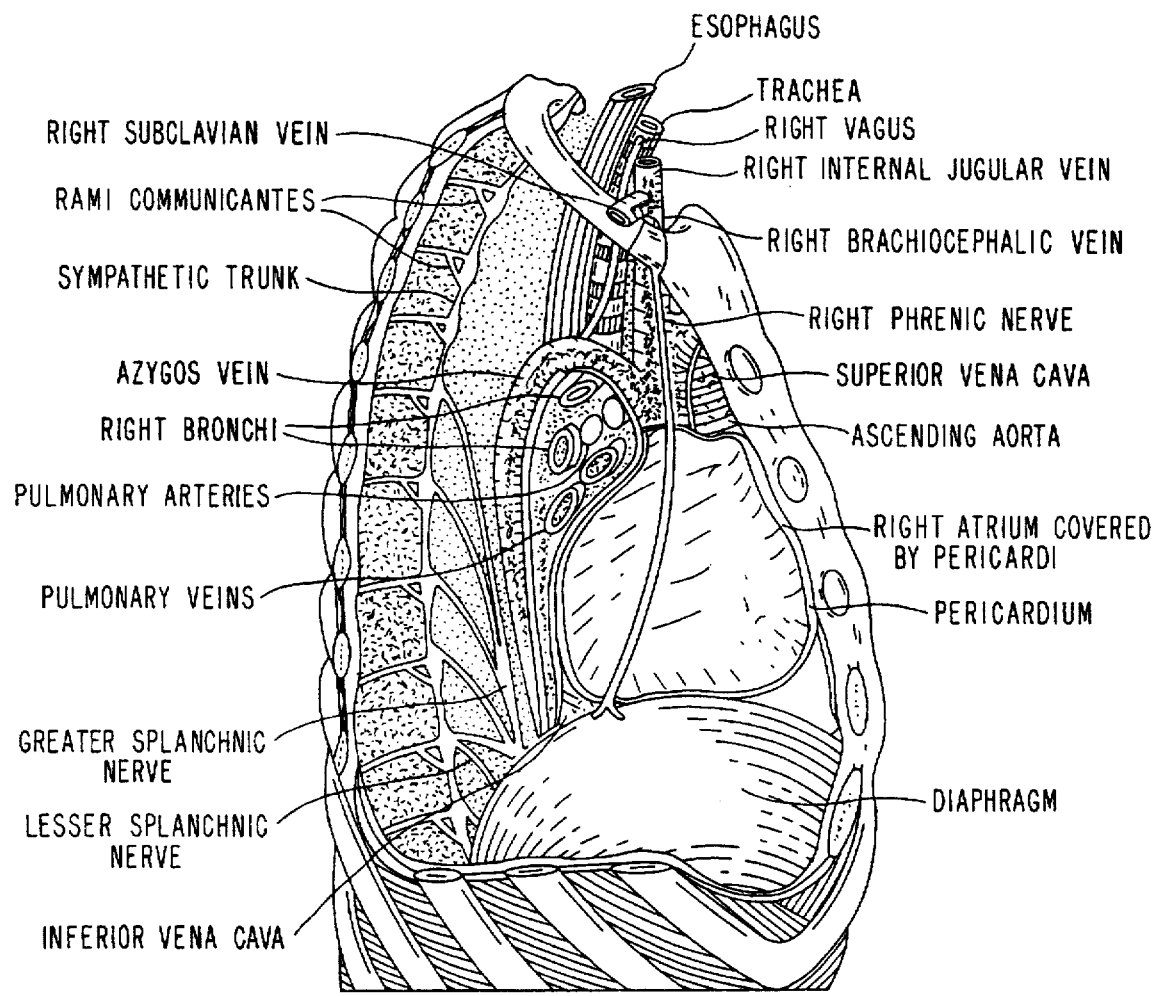
FIG. 8 is a depiction of the organs and human skeleton taken as a right side mediastinum section depicting the relative locations of the pericardial sac, the diaphragm, the azygos vein, the rib cage and the associated external and internal intercostal muscles.

Turning now to FIG. 8, the orientation of the internal organs to the rib cage and respiratory muscle system depicted in FIG. 7A to 7C is depicted in a right side mediastinum view. FIG. 8 shows a relative orientation of the heart, the diaphragm, the great veins, the rib cage and the internal and external intercostal muscles. The specific pacing systems of FIGS. 9 to 13 are designed to take advantage of the relative locations of the skeletal respiratory muscles, the diaphragm, the heart and the venous system.

Specific System Configurations

Normally pacing pulse generators are placed under the skin in the pectoral region outside the rib cage so that the transvenous pacing lead may be introduced into the right heart through the right subclavian vein or the right internal jugular vein, through the superior vena cava, into the right atrium, through the tricuspid valve and into the right ventricle for ventricular pacing systems. In accordance with the present invention, that conventional pacemaker system and implantation technique may be employed in conjunction with an additional lead and electrode coupled to the connector block of the pacemaker and transvenously advanced through the right subclavian vein or right internal jugular vein into the upper portion of the superior vena cava and then into the azygos vein and advanced to a position adjacent to the surface of the intercostal muscle sheath and the diaphragm. Such an introduction and orientation of the electrode systems is depicted schematically in FIG. 9.

Figure 9:
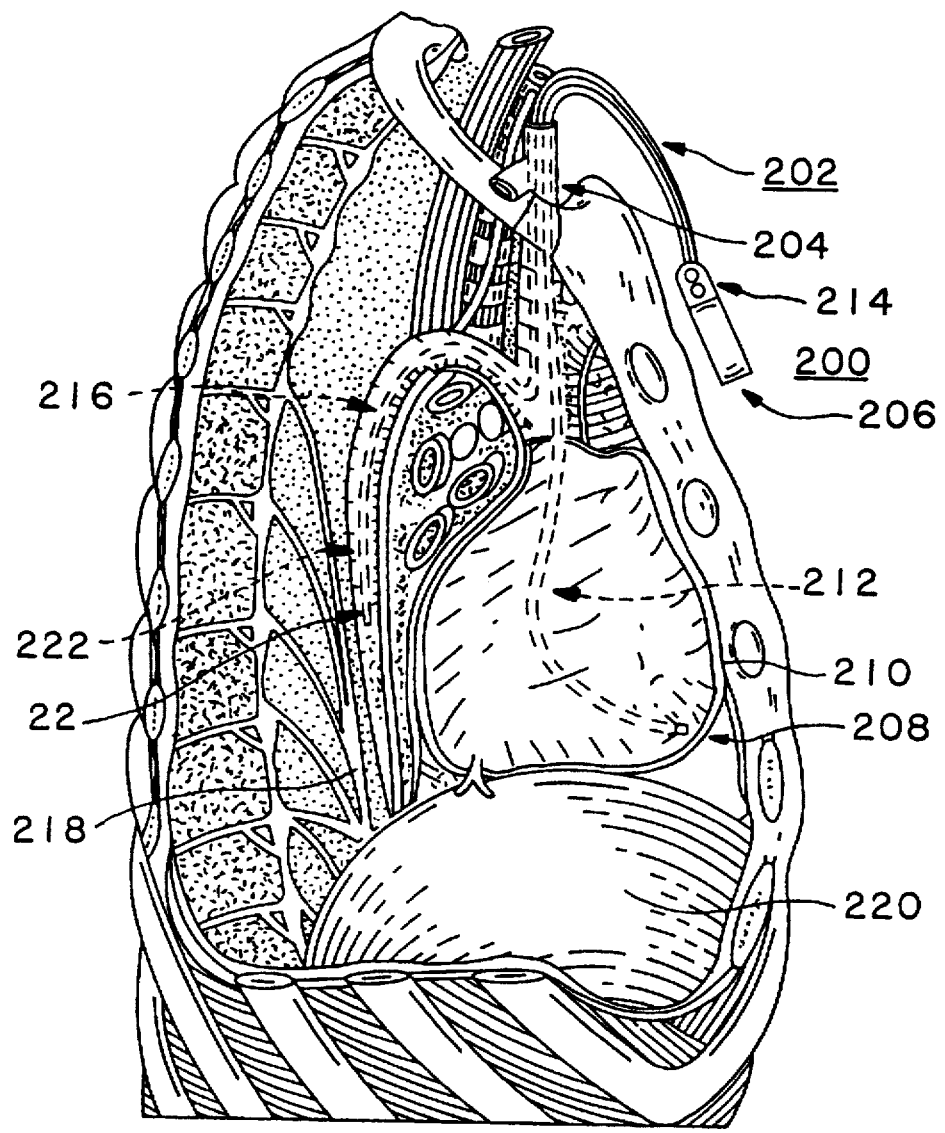
FIG. 9 is a schematic illustration of a first embodiment of a pacing system incorporating the EMG signal processing concepts of the present invention having a conventional pace and sense lead system in conjunction with an EMG lead system residing in the azygos vein.

In FIG. 9, the pacemaker pulse generator 200 and lead system 202 are shown in a typical implantation location outside the breastbone and lying under the patient's skin with the lead system 202 extending into the right internal jugular vein 204. The pacing pulse generator 200 includes an electrically conductive case 206 which may act as the indifferent pace/sense electrode in conjunction with the active pace/sense electrode 208 extending into the right ventricle of the patient's heart 210 at the tip of lead 212. Lead 212 is coupled to the pulse generator 200 at connector block 214 in a fashion well known in the art.

In accordance with the present invention, the lead system 202 includes the azygos vein lead 216 which is also introduced into the right internal jugular vein and advanced into the superior vena cava and rotated under fluoroscopic control to be directed into the azygos vein and to be advanced in the upstream direction in the azygos vein to a position adjacent to the surface of the intercostal muscle sheath depicted generally at 218 in the diaphragm depicted generally at 220. The azygos vein lead 216 carries a pair of spaced apart EMG sensing electrodes 222 and 224, which are constructed in the same fashion as a bipolar pacemaker pace/sense lead and electrode. In use, the EMG signal from the respiratory muscles is picked up across the electrodes 222 and 224 and conducted through conductors within lead 216 back to the pulse generator 200 for processing in the manner described hereinbefore.

Although not specifically shown, the embodiment of FIG. 9 may employ one or more Medtronic Model 4951 type electrodes hooked into respiratory muscle tissue in the vicinity of the surgical implant of the pulse generator rather than employing the azygos vein lead. In those instances where the surgeon finds it convenient to implant epicardial pacing leads near the apex of the heart 210 of FIG. 9, the diaphragm 220 will be exposed in the limited thoracotomy procedure to place the leads and either suture style or hooking electrode leads may be placed directly in the diaphragm muscle 220. In such a procedure, the pacing pulse generator 200 would be implanted subcutaneously in the abdominal region, rather than pectorally as shown in FIG. 9.

The orientation of the heart to the diaphragm as depicted in FIG. 9 provides the opportunity to employ, in open chest surgical procedures, a pacing system extending between the epicardium of the patient's heart to the surface of the diaphragm. The proximity of the heart to the diaphragm allows for the use of a connectorless pacing system having a pulse generator and electrode system adapted to be directly coupled to either the epicardium or the diaphragm along with a short lead and electrode system which may be surgically attached to the other of the two organs. Two embodiments of such pacing systems are depicted schematically in FIG. 10.

Figure 10:
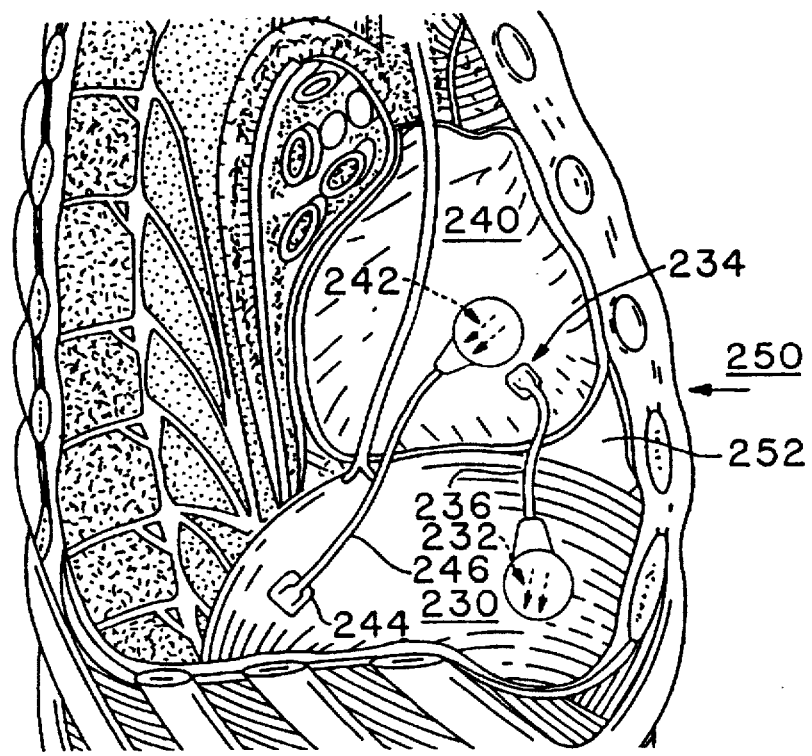
FIG. 10 is a schematic illustration of second and third embodiments of the interconnection of pacing systems between the myocardium of the patient's heart and the diaphragm.

The first embodiment depicted in FIG. 10 comprises the pacemaker pulse generator 230, EMG sense electrodes 232, pace/sense electrodes 234 and lead extension 236 extending between the pulse generator 230 and the pace/sense electrodes 234. The second embodiment depicted in FIG. 10 comprises the pulse generator 240, the pace/sense electrodes 242, the EMG sense electrodes 244 and the lead extension 246 extending between the EMG electrodes 244 and the pulse generator 240. It is anticipated that one or the other of the two embodiments depicted in FIG. 10 would be employed in a surgical procedure that involves a mediasternal incision and limited thoracotomy conducted in the direction of the arrow 250 to expose the space 252. For convenience of illustration, the pacing systems are shown displaced from space 252. Whether the system of the second or the third embodiment is implanted, it is also understood that the pericardial sac surrounding the heart would be exposed in that procedure in order to affix the electrodes 234 of the second embodiment or the electrodes 242 and pulse generator 240 of the third embodiment directly to the ventricular myocardium and that the pericardial sac would be sutured back together leaving only the lead bodies 236, 246 extending out of the enclosed pericardial sac and toward the diaphragm.

In the embodiments depicted in FIG. 10, it is contemplated that hooking electrode pairs be employed as the electrodes 232, 234 and 242, 244, although it would be understood that spiral screw-in electrodes of the Medtronic Model 6917 type or of the type depicted in U.S. Pat. Nos. 4,157,720 and 4,256,115, incorporated herein by reference, could be employed at least for electrodes 234 or 242 where the myocardial screw-in electrodes made by a purchase in the relatively thick myocardium sufficient to support the pulse generator without penetrating therethrough. In the fixation of the electrodes 232 and 244 to the diaphragm, it is anticipated that hooking electrodes of the type described hereinabove would be employed due to their relatively shallow penetration depth. In addition, it is anticipated that it may be necessary to suture the pulse generator cases 230, 240 in the electrodes 234, 244 in position for added purchase.

In view of the relatively short distance between the epicardial surface of the heart and the diaphragm, it is contemplated that the pulse generator and lead assembly be constructed without a connector block, at least in the case of the third embodiment where the addition of a connector block adds to the bulk of the pulse generator. In view of the close distances between the myocardium and the diaphragm and the absence of any need to employ a stylet to place the leads 236, 246, the pacing system in either case may employ permanently attached and connectorless lead systems.

Figure 11:
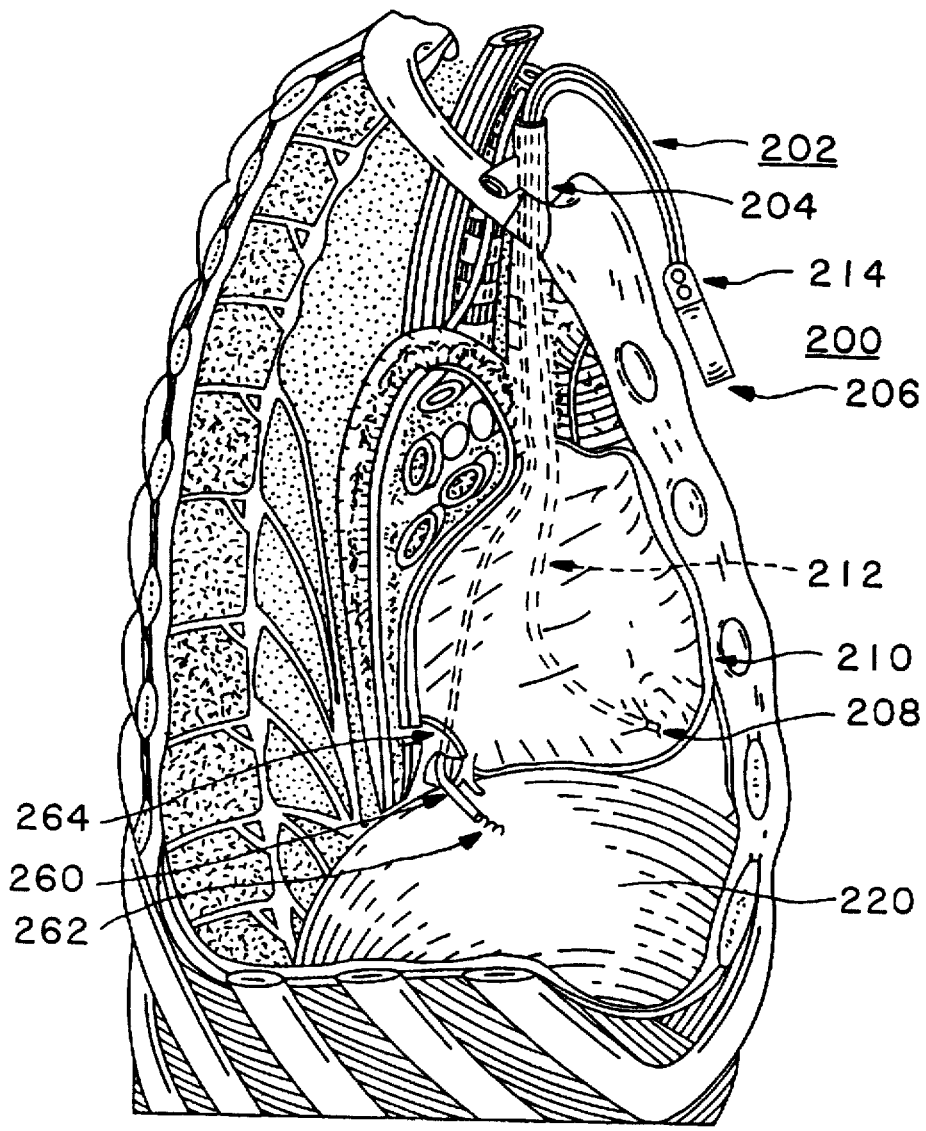
FIG. 11 is a schematic illustration of a further embodiment of the interconnection of a conventionally implanted pacemaker and pace and sense lead system in conjunction with an EMG lead and electrode extending through a vein wall and attached to the diaphragm.
Figure 12:
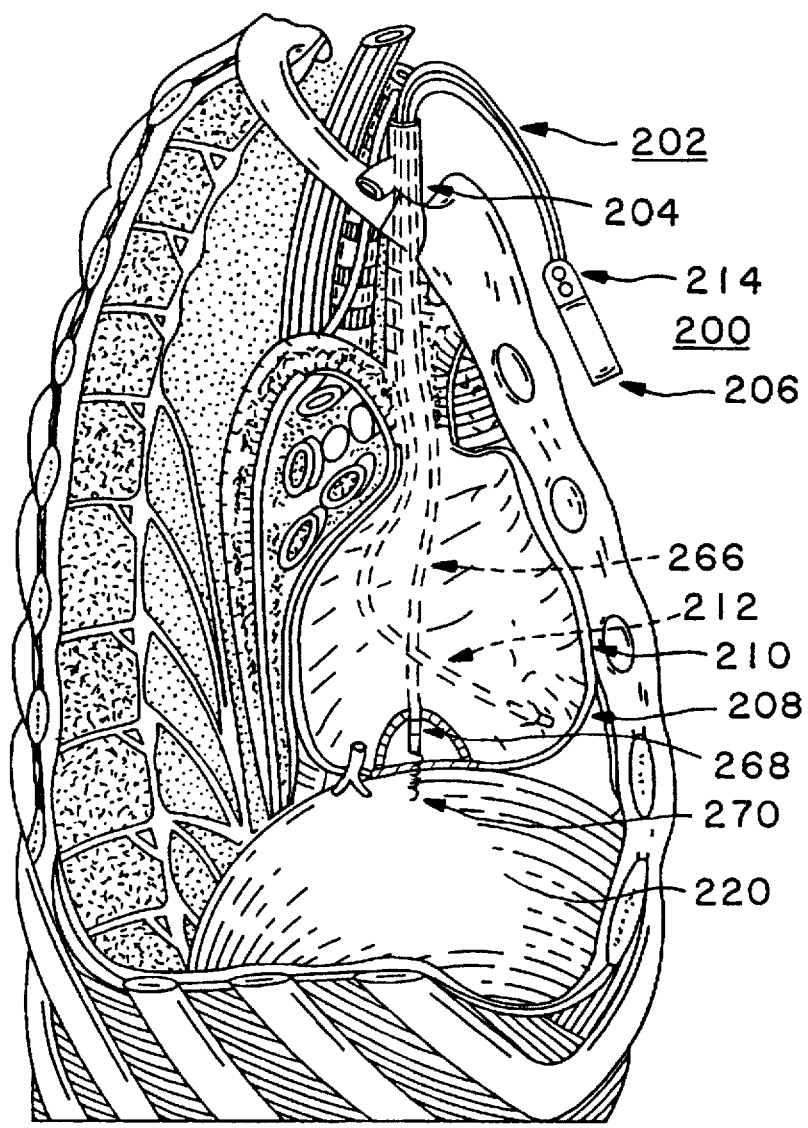
FIG. 12 is a schematic illustration of a further embodiment of the interconnection of a conventionally implanted pacemaker and pace and sense lead system in conjunction with an EMG lead and electrode extending through the atrial myocardium and attached to the diaphragm.
Figure 13:
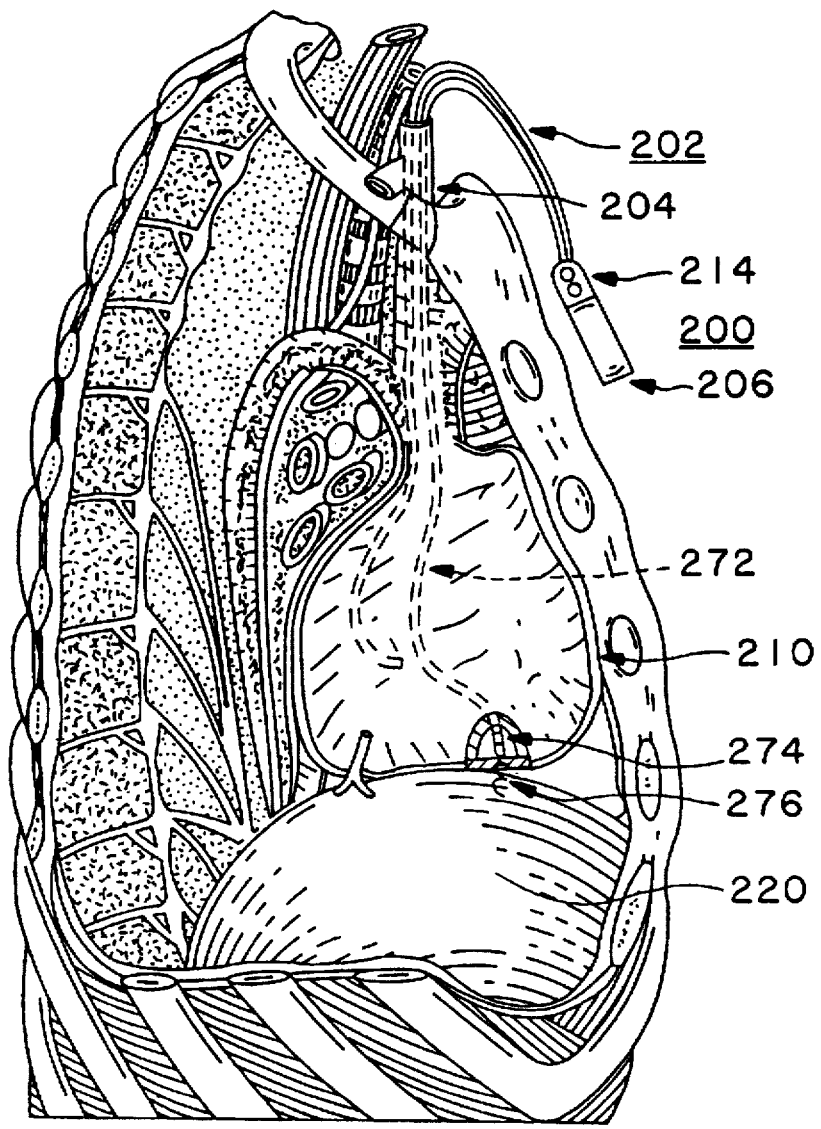
FIG. 13 is a schematic illustration of a further embodiment of the interconnection of a conventionally implanted pacemaker and pace and sense lead system in conjunction with an EMG lead and electrode extending through the ventricular myocardium and attached to the diaphragm.

Turning now to FIGS. 11 to 13, three further embodiments of the EMG sensing and rate responsive pacing and electrode system of the present invention are depicted where advantage is taken of the tendency of the low pressure right atrium, ventricle and venous system to self-seal punctures through the myocardial and venous walls, particularly if the puncturing instrument is left in place. It has been reported in the literature that pacing leads have been inadvertently passed through the right ventricular apex myocardium and into contact with the diaphragm, causing it to contract and the patient to hiccup each time a pacing pulse is emitted. In such cases, the unintentional penetration does not result in catastrophic bleeding as the myocardium tends to bear against the lead body and seal the puncture at the relatively low venous pressure. Similarly, it is possible to puncture and pass a lead through the atrial myocardial wall or a vein with minimal bleeding followed by sealing, as long as the lead is relatively stable.

In the embodiment of FIG. 11, the pacemaker 200, 206, 214 and pacing lead system 202, 208, 212 are implanted and connected together as described in conjunction with FIG. 9. However, the EMG sensing lead 260, having a screw-in electrode 262 at its distal tip, is passed transvenously with lead 212 into the superior vena cava, but then through an opening in the inferior vena cava 264, just below the heart 210 and near the diaphragm 220. Thus, the lead 260 by-passes the right atrium and ventricle, extending from the superior vena cava and into the inferior vena cava, where it exits the vessel and is screwed into the diaphragm.

The penetration of the inferior vena cava is preferably accomplished by the sharp tip of the screw-in electrode 262 itself. With a small diameter lead body, the tip electrode 262 and lead body may be extended through the opening and screwed into the diaphragm, leaving a length of the lead 260 in the space between the pericardial sac and the diaphragm to allow for its respiratory movement. After a short time, the wound made by the lead through the vein wall will seal. Alternatively, it may be possible to rotate the screw-in electrode through the venous wall and directly into the adjacent diaphragm to attach them together and to rely on fibrosis to hold then together chronically.

In FIG. 12, a reduced diameter extension of an atrial lead 266 having an atrial pace and sense electrode 268 constitutes the screw-in EMG sense electrode 270'. In this embodiment, the electrode 270 is screwed through the thin atrial myocardium and the pericardial sac from inside the right atrium and then screwed into the adjoining diaphragm. Since the heart 210 rests on the diaphragm and follows diaphragm movement in respiration, it is possible to fix the electrode 270 while retaining the electrode 268 within the right atrium. The fixation through the atrial myocardium is illustrated in the cut-out section of heart 210.

The pacing system depicted in FIG. 12 is a dual chamber pacemaker having a second lead 212 positioned in the right ventricle. The embodiments of FIGS. 9 and 11 may likewise be implemented in a dual chamber pacing system.

In FIG. 13, a reduced diameter extension of a ventricular lead 272 having a ventricular pace and sense electrode 274 constitutes the screw-in EMG sense electrode 276. In this embodiment, the electrode 276 is screwed through the relatively thicker right ventricular myocardium and the pericardial sac from inside the right ventricular and directly into the adjoining diaphragm. As in the atrial embodiment of FIG. 12, it is expected that chronic tissue fibrosis will occur in the area that the screw-in electrode 276 so-acutely attaches heart 208 to these diaphragm 220. However, with only a small portion of the screw-in electrode 276 exposed, it will be able to pick up the diaphragm EMG in distinction to the cardiac ECG. The fixation is again illustrated by a cut-out section of heart 210.

The EMG sensing leads 260, 266, 272 and electrodes 262, 270, 276 of FIGS. 11–13 may be implemented in either unipolar or bipolar electrode configurations. The fixation of the electrodes may be accomplished by means other than the corkscrew electrodes depicted, e.g., by hooks, barbs, open helixes, or spreading wires, for active fixation, or by surface modification of the electrodes to promote tissue ingrowth, for passive fixation. Bipolar screw-in electrodes may be effected by providing insulated coaxial multi-filar conductors having spaced apart uninsulated turns. Thus, the entire single pass lead 222 of the FIG. 13 embodiment may include up to four separately insulated, co-axial, multi-filer conductors connected to bipolar pace/sense electrodes 274 and EMG electrodes 276 or even include two more such conductors and a pair of atrial pace and sense electrodes. In all cases, the EMG sensing electrodes and the pace/sense electrodes must be insulated from one another and kept away from the diaphragm and myocardium, respectively, to simplify EMG and ECG-sensing.

If electrodes 262, 270, 276 are not designed to penetrate the vein wall or myocardium themselves, conventional tissue coring catheters may be first inserted to the desired location and used to make a hole for their passage.

Although not specifically depicted in the drawings, it is further contemplated that the pacing systems of the type shown in FIG. 10 may also employ a pulse generator having first and second sets of electrodes for placement epicardially on the patient's heart and separately on the diaphragm with the pulse generator situated in the pocket 252 or outside the rib cage in conventional fashion. The embodiments depicted in FIGS. 9–12 are illustrative of the various ways in which the EMG electrodes may be coupled with the pacing system to pick up the respiratory muscle EMG and conduct it to the pulse generator. In accordance with the present invention, the signals are processed employing the moving time averages of the selected signals described above to develop the pacing rate control system.

Several modifications of the configurations of the pacing systems of the present invention may become readily apparent to those skilled in the art in light of the foregoing disclosure. Therefore, the scope of the present invention should be interpreted solely from the following claims, as such claims are read in light of the disclosure.

What is claimed is:

1. A rate responsive demand pacemaker comprising:
    means for pacing a patient's heart at a controlled rate modifiable by a rate control signal at the end of a pacing escape interval in the absence of a sensed natural depolarization of the heart;
    means for sensing natural depolarizations of the heart and resetting said escape interval;
    electrode and conductor means for coupling said pacing and sensing means to myocardial tissue for conducting pacing pules to the patient's heart and including natural electrical depolarizations of the patient's heart to said sensing means;
    an electrode means, for conducting electromyogram signals generated in the respiratory musculature in conjunction with respiration to said pacing means; and
    signal processing means responsive to said electromyogram signals for determining the respiratory minute ventilation through moving time average signal processing of the recurring electromyogram signals,
    wherein said electromyogram signal processing means further comprises:
        means for amplifying and bandpass filtering the electromyogram signal;
        means for rectifying and moving time average processing the amplified and bandpass filtered electromyogram signal;
        means for determining values for three time signals; the inspiratory time, expiratory time, and total breath time of successive moving time average processed electromyogram signals so as to employ one or a combination of said three time signals as said minute ventilation variable.

2. A rate responsive demand pacemaker in accordance with claim 1 wherein said means for determining the inspiratory time, expiratory time, and total breath time further comprises:
    means for developing the moving time averages of the slope of the amplified and bandpass filtered electromyogram signal during the inspiratory time phase;
    means for developing a moving time average of the peak amplitude value of the processed electromyogram signal; and
    means for employing the moving time average slope and peak values to set a first threshold value and a second threshold value for determining the beginning of the inspiratory time when the subsequent processed electromyogram signals exceed the first threshold and the end of the inspiratory time when the peak amplitude of the processed electromyogram signal falls below the second threshold, whereby the inspiratory time may be determined by the elapsed time between subsequent excursions of the processed electromyogram signal through said first and second threshold values and said expiratory time may be determined from the time elapsed between successive excursions of the processed electromyogram signal between said second and said first threshold value.

3. A rate responsive demand pacemaker in accordance with claim 1 further comprising:
    means for establishing said pacing escape interval corresponding in time to a nominal standby pacing rate;
    means providing a sense event signal upon sensing electrical depolarizations of the patient's heart;
    means responsive to said sense event signal for resetting said escape interval;
    means responsive to the time-out of said escape interval for delivering a pacing pulse to the patient's heart;
    means responsive to said rate control signal for changing the pacemaker's nominal standby rate by increasing or decreasing the nominal escape interval, and wherein:
        said signal processing means further comprises means responsive to delivery of a pacing impulse or the occurrence of a sense event signal for inhibiting the sensing of the electromyogram signal for a predetermined blanking interval encompassing the delivery of the pacing pulse to or the sensing of the depolarization wave of the heart.

4. A rate responsive demand pacemaker in accordance with claim 2 wherein:

said pacing means further comprises a case having at least one first electrode means extending therefrom adapted for active fixation to body tissue with respiratory musculature tissue and a lead extending from said case bearing a second electrode means adapted for active fixation to body tissue closely associated with the cardiac muscle; and wherein said pacing case first electrode means is adapted to be coupled to respiratory musculature and said second electrode means are adapted to be attached to the patient's heart.

5. A rate responsive demand pacemaker in accordance with claim 2 wherein:

said pacing means further comprises a case having at least one first electrode means extending therefrom adapted for active fixation to body tissue and a further electrode means on a lead extending from said case and bearing a second electrode means for active fixation to body tissue; and wherein said first and further electrode means are adapted to be coupled electrically to the patient's heart and to the patient's respiratory musculature, respectively.

6. A rate responsive demand pacemaker comprising:

means for pacing a patient's heart at a controlled pacing rate;

a pair of spaced electrode means, at least one of said pair adapted to be placed in a blood vessel in the vicinity of the patient's respiratory musculature;

means coupled to said electrode means for sensing the electromyogram of the respiratory musculature associated with inspiration and/or expiration;

means for processing the electromyogram signal for providing a rate control measure in the form of a rate control signal the value of which is representative of the patients's minute ventilation;

said electromyogram signal processing means further comprising:

means for amplifying and bandpass filtering the electromyogram signal;

means for rectifying and moving time average processing the amplified and bandpass filtered electromyogram signal;

means for determining a value for the inspiratory time, expiratory time, and total breath time of successive moving time average processed electromyogram signals; and means for developing said rate control signal as a function of at least one of said inspiratory time, expiratory time, and total breath time values.

7. A rate responsive demand pacemaker in accordance with claim 8 wherein said means for determining the inspiratory time, expiratory time, and total breath time values further comprises:

means for developing the moving time averages of the slope of the amplified and bandpass filtered electromyogram signal during the inspiratory time phase;

means for developing a moving time average of the peak amplitude value of the processed electromyogram signal; and means for employing the moving time average slope and peak values to set a first threshold value and a second threshold value for determining the beginning of the inspiratory time when the subsequent processed electromyogram signals exceed the first threshold and the end of the inspiratory time when the peak amplitude of the processed electromyogram signal falls below the second threshold, whereby the inspiratory time may be determined by the elapsed time between subsequent excursions of the processed electromyogram signal through said first and second threshold values and said expiratory time may be determined from the time elapsed between successive excursions of the processed electromyogram signal between said second and said first threshold value.

8. A rate responsive demand pacemaker in accordance with claim 7 further comprising:

means for establishing said pacing escape interval corresponding in time to a nominal standby pacing rate;

means providing a sense event signal upon sensing electrical depolarizations of the patient's heart;

means responsive to said sense event signal for resetting said escape interval;

means responsive to the time-out of said escape interval for delivering a pacing pulse to the patient's heart;

means responsive to said rate control signal for changing the pacemaker's nominal standby rate by increasing or decreasing the nominal escape interval, and wherein:

said signal processing means further comprises means responsive to delivery of a pacing impulse or the occurrence of a sense event signal for inhibiting the sensing of the electromyogram signal for a predetermined blanking interval encompassing the delivery of the pacing pulse to or the sensing of the depolarization wave of the heart.

9. A rate responsive demand pacemaker comprising:

means for pacing a patient's heart at a controlled pacing rate responsive to a rate control signal value comprising a pulse generator, and an escape interval timing means, for providing pacing pulses from said pulse generator at a rate determined by and having timeouts measured by said escape interval timing;

pacing lead means extending from a main housing of said pulse generator to a patient's heart and having at least one pacing and sensing electrode for applying pacing pulses to the heart and sensing electrical heart signals therefrom;

EMG sensing lead with electrode means deposed thereon for positioning at least one sensing electrode adjacent to or embedded into a respiratory muscle and conducting EMG signal from such an adjacent or embedded position to said pacemaker, said lead adapted to be placed within a blood vessel at a point adjacent to said pulse generator, extend through a predetermined path within the patient's venous system and to exit the venous system and to exit the venous system at a point adjacent to selected respiratory musculature to place said electrode adjacent to or into the selected respiratory musculature;

means for processing the EMG signals for providing said rate control signal value representative of the patient's minute ventilation comprising;

means for amplifying and bandpass filtering the EMG signal;

means for rectifying and moving time average processing said amplified and bandpass filtered EMG signal;

means for determining the inspiratory time, expiratory time, and total breath time of successive moving time average processed EMG signals; and means for employing the value of a function of at least one of said inspiratory time, expiratory time, and total breath time values as said rate control signal.

10. A rate responsive demand pacemaker in accordance with claim 9 wherein said means for determining the inspiratory time, expiratory time, and total breath time further comprises:

means for developing the moving time averages of the slope of the amplified and bandpass filtered EMG signal during the inspiratory time phase;

means for developing a moving time average of the peak amplitude value of the processed EMG signal; and means for employing the moving time average slope and peak values to set a first threshold value and a second threshold value for determining the beginning of the inspiratory time when the subsequent processed EMG signals exceed the first threshold and the end of the inspiratory time when the peak amplitude of the processed EMG signal falls below the second threshold, whereby the inspiratory time may be determined by the elapsed time between subsequent excursions of the processed EMG signal through said first and second threshold values and said expiratory time may be determined from the time elapsed between successive excursions of the processed EMG signal between said second and said first threshold value.

11. A rate responsive demand pacemaker in accordance with claim 10 further comprising:

means for establishing said pacing escape interval corresponding in time to a nominal standby pacing rate;

means providing a sense event signal upon sensing electrical depolarizations of the patient's heart;

means responsive to said sense event signal for resetting said escape interval;

means responsive to the time-out of said escape interval for delivering a pacing pulse to the patient's heart;

means responsive to said rate control signal for changing the pacemaker's nominal standby rate by increasing or decreasing the nominal escape interval, and wherein:

said signal processing means further comprises means responsive to delivery of a pacing impulse or the occurrence of a sense event signal for inhibiting the sensing of the EMG signal for a predetermined blanking interval encompassing the delivery of the pacing pulse to or the sensing of the depolarization wave of the heart.

12. A rate responsive demand pacemaker comprising:

means for pacing a patient's heart at a controlled pacing rate responsive to a rate control signal value comprising a pulse generator, and escape interval timing means, for providing pacing pulses from said pulse generator at an rate determined by and having timeouts measured by said escape interval timing means and pacing lead means adapted to extend from said pulse generator to a patient's heart in a manner so as to have at least one pacing and sensing electrode for applying pacing pulses to the heart and for sensing electrical heart signals therefrom;

EMG sensing lead means coupled to said pacing lead means and comprising at least one EMG electrode positioned on a distal section of said pacing lead means and at least one insulated EMG sense conductor extending from said EMG electrode to the proximal end of said pacing lead means for conducting EMG signals to said pulse generator, wherein said pacing lead means is adapted to be placed transvenously into the ventricle of the patient's heart and further comprises at least one insulated pace and sense conductor extending from said pace and sense electrode to said pulse generator, and wherein said EMG sensing lead means is adapted to be extended through the myocardial wall from the interior of the ventricle to the exterior thereof for positioning said distal section of said pacing lead means and EMG sensing electrode or electrodes in contact with the patient's diaphragm for sensing the EMG of the diaphragm associated with inspiration;

means for processing the EMG signals for providing a rate control signal value representative of the patient minute ventilation comprising;

means for amplifying and bandpass filtering the EMG signal;

means for rectifying and moving time average processing the amplified and bandpass filtered EMG signal;

means for determining values for the inspiratory time, expiratory time, and total breath time of successive moving time average processed EMG signals; and means for employing the value of a function of at least one of said inspiratory time, expiratory time, and total breath time values as said rate control signal.

13. A rate responsive demand pacemaker in accordance with claim 12 wherein said means for determining the inspiratory time, expiratory time, and total breath time further comprises:

means for developing the moving time averages of the slope of the amplified and bandpass filtered EMG signal during the inspiratory time phase;

means for developing a moving time average of the peak amplitude value of the processed EMG signal; and means for employing the moving time average slope and peak values to set a first threshold value and a second threshold value for determining the beginning of the inspiratory time when the subsequent processed EMG signals exceed the first threshold and the end of the inspiratory time when the peak amplitude of the processed EMG signal falls below the second threshold, whereby the inspiratory time may be determined by the elapsed time between subsequent excursions of the processed EMG signal through said first and second threshold values and said expiratory time may be determined from the time elapsed between successive excursions of the processed EMG signal between said second and said first threshold value.

14. A rate responsive demand pacemaker in accordance with claim 13 further comprising:

means for establishing said pacing escape interval corresponding in time to a nominal standby pacing rate;

means providing a sense event signal upon sensing electrical depolarizations of the patient's heart;

means responsive to said sense event signal for resetting said escape interval;

means responsive to the time-out of said escape interval for delivering a pacing pulse to the patient's heart;

means responsive to said rate control signal for changing the pacemaker's nominal standby rate by increasing or decreasing the nominal escape interval, and wherein:

said signal processing means further comprises means responsive to delivery of a pacing impulse or the occurrence of a sense event signal for inhibiting the sensing of the EMG signal for a predetermined blanking interval encompassing the delivery of the pacing pulse to or the sensing of the depolarization wave of the heart.

15. A heart pacemaker having a sensing lead for measuring EMG from the respiration musculature of a patient further comprising:

a signal interpretation means for determining from signals to be received from said sensing lead and to provide a moving time average value of an EMG;

a processing means for determining from said moving time average values, values for average slope, maximal slope and/or delta;

a threshold value holding means for setting first and second threshold values;

inspiratory time measurement means for determining either or both of the following defined values;

(a) the beginning of inspiratory time ("BIT") as being when subsequent processed EMG signals amplitude exceeds said first threshold and (b) the end of inspiratory time ("EIT") as when the EMG signal amplitude falls below said second threshold; and ventilation rate processor means for determining ventilation rate based on the amount of time between either a first and a next subsequent EIT or between a first and a next subsequent BIT.

16. A pacemaker as set forth in claim 15 wherein said ventilation rate processor means further comprises:

tidal volume index means for providing a value based on one or a combination of said average slope, maximal slope, or delta values, means for determining total breath time from said EIT and/or BIT times; and dividing the tidal volume index value by the total breath time so as to generate a value corresponding to minute ventilation.

17. A pacemaker as set forth in claim 16 wherein said value corresponding to minute ventilation is updated by a means for updating said value which determines whether to update said value breath by breath.

18. The pacemaker of claim 15 wherein said ventilation rate processor means provides a signal value to a pacing rate determining processor for adjusting the timing of pacing pulses based upon said determined ventilation rate.

19. A rate responsive demand pacemaker in accordance with claim 15 wherein:

said pacing means further comprises a case having at least one first electrode means extending therefrom adapted for active fixation to body tissue and a further electrode means on a lead extending from said case and bearing a second electrode means for active fixation to body tissue; and wherein said first and further electrode means are adapted to be coupled electrically to the patient's heart and to the patient's respiratory musculature, respectively.

20. A rate responsive demand pacemaker having a rate determining processor for pacing a patient's heart at a controlled rate modifiable by a rate control signal at the end of a pacing escape interval in the absence of a sensed natural depolarization of the heart; means for sensing natural depolarizations of the heart and resetting said escape interval; electrode and conductor means for coupling said pacing and sensing means to myocardial tissue for conducting pacing pulses to the patient's heart and conducting natural electrical depolarizations of the patient's heart to said sensing means; a lead for fixation to respiratory musculature and means for reading an EMG therefrom and having EMG processing means, said EMG processing means for determining the respiratory minute ventilation further comprising:

means for amplifying and bandpass filtering the electromyogram signal;

means for rectifying and moving time average processing the amplified and bandpass filtered electromyogram signal;

means for determining an average slope, peak slope and/or delta values of said moving time average EMG signal;

means for determining a tidal volume index value based on said average slope, peak slope and/or delta values of said moving time average EMG signal, and means for developing said rate control signal as a function of the relationship of said tidal volume index and said total breath time.

21. A rate responsive demand pacemaker comprising:

means for pacing a patient's heart at a controlled rate modifiable by a rate control signal at the end of a pacing escape interval in the absence of a sensed natural depolarization of the heart;

means for sensing natural depolarizations of the heart and resetting said escape interval having means for timing said escape interval;

electrode and conductor means for coupling said pacing and sensing means to myocardial tissue for conducting pacing pules to the patient's heart and including natural electrical depolarizations of the patient's heart to said sensing means;

an electrode means, for conducting electromyogram signals generated in the respiratory musculature in conjunction with respiration to said pacing means; and signal processing means responsive to said electromyogram signals for determining the respiratory minute ventilation through moving time average signal processing of the recurring electromyogram signals wherein said electromyogram signal processing means further comprises:

means for amplifying and bandpass filtering the electromyogram signal;

means for rectifying and moving time average processing the amplified and bandpass filtered electromyogram signal;

means for determining values for successive moving time average processed electromyogram signals on a breath by breath basis;

means for determining a tidal volume index value based on average slope, peak slope and/or delta values of said moving time average EMG signal, means for determining total breath time based on said total index signals, and means for developing said rate control signal as a function of the relationship of said tidal volume index and said total breath time.

22. A rate responsive demand pacemaker in accordance with claim 21 wherein:

said pacing means further comprises a case having at least one first electrode means extending therefrom adapted for active fixation to body tissue with respiratory musculature tissue and a lead extending from said case bearing a second electrode means adapted for active fixation to body tissue closely associated with the cardiac muscle; and wherein said pacing case first electrode means is adapted to be coupled to respiratory musculature and said second electrode means are adapted to be attached to the patient's heart.

* * * * *